(12) United States Patent
King et al.

(10) Patent No.: US 6,872,562 B2
(45) Date of Patent: Mar. 29, 2005

(54) HERBICIDE RESISTANT DINITROGEN FIXING BACTERIA AND METHOD OF USE

(75) Inventors: Charles A. King, Fayetteville, AR (US); Larry C. Purcell, Fayetteville, AR (US)

(73) Assignee: The Board of Trustees of the University of Arkansas, N.A., Little Rock, AR (US)

( * ) Notice: Subject to any disclaimer, the term of this patent is extended or adjusted under 35 U.S.C. 154(b) by 0 days.

(21) Appl. No.: 10/050,593

(22) Filed: Jan. 16, 2002

(65) Prior Publication Data

US 2002/0152503 A1 Oct. 17, 2002

Related U.S. Application Data

(60) Provisional application No. 60/262,241, filed on Jan. 16, 2001.

(51) Int. Cl.[7] .................................................. C12N 1/21
(52) U.S. Cl. ........................ 435/252.2; 435/4; 435/7.32; 435/34; 435/440; 435/441; 435/468; 435/471; 435/476; 435/243; 435/244; 435/410; 435/418; 435/426; 435/415; 435/320.1; 536/23.1; 536/23.2; 536/23.7
(58) Field of Search ............................ 435/4, 7.32, 34, 435/440, 441, 468, 471, 476, 243, 244, 410, 418, 426, 415, 252.2, 320.1; 536/22.1, 23.1, 23.2, 23.7

(56) References Cited

U.S. PATENT DOCUMENTS 6,407,316 B1 * 6/2002 Holmes et al.
2002/0058327 A1 * 5/2002 Loh et al.

OTHER PUBLICATIONS

No additional references are cited by the Examiner.*
Jaworski; Mode of Action of N–Phosphonomethylglycine: Inhibition of Aromatic Amino Acid Biosynthesis; J. AGR. Food Chem; vol. 20, No. 6, 1972; pp. 1195–1198. Monsanto Company, Agricultural Division, St. Louis, Missouri 63166.

Moorman et al. Production of Hydroxybenzoic Acids by *Bradyrhizobium japonieum* Strains after Treatment with Glyphosate; J. AGR. Food Chem; vol. 40, 1992, pp. 289–293. American Chemical Society.

Streeter; Failure of Inoculent Rhizobia to Overcome the Dominance of Indigenous Strains for Nodule Formation; Can. J. Microbiol; vol. 40, 1994, pp. 513–522.

Delannay et al. Yield Evaluation of a Glyphosate–Tolerant Soybean Line after Treatment with Glyphosate; Crop Sci; vol. 35, 1995, pp. 1461–1467.

Devine et al. Host Genetic Control of Symbiosis in Soybean (*Glycine max* L.). Plant and Soil; vol. 186, 1996, pp. 173–187.

Hoagland et al. Effects of Glyphosate on *Bradyrhizobium japonicum* Interactions in Roundup–Ready Soybeans. WSSA Abstracts; 1999 Meeting of the Weed Science Society of America, vol. 39; p. 38. San Diego, California.

Reddy et al. Effect of Glyphosate on Growth, Chlorophyll, and Nodulation in Glyphosate–Resistant and Susceptible Soybean (*Glycine max*) Varieties. Journal of New Seeds, vol. 2(3), 2000, pp. 37–52.

* cited by examiner

*Primary Examiner*—James Ketter
*Assistant Examiner*—David A. Lambertson
(74) *Attorney, Agent, or Firm*—Jondle & Associates P.C.

(57) ABSTRACT

The present invention is directed to herbicide resistant $N_2$ fixing bacteria. The bacteria are useful for effecting $N_2$ fixation, nodulation, growth and yield of herbicide resistant or tolerant leguminous plants treated with herbicide. The bacteria are particularly useful for providing competitive advantage to superior $N_2$ fixing rhizobial strains over non-resistant indigenous rhizobia for nodulation of herbicide resistant or tolerant leguminous plants.

29 Claims, 10 Drawing Sheets

HERBICIDE RESISTANT DINITROGEN FIXING BACTERIA AND METHOD OF USE

CROSS REFERENCE

This application is related to U.S. Provisional Application, Ser. No. 60/262,241, filed Jan. 16, 2001, incorporated herein by reference.

BACKGROUND OF THE INVENTION

This invention relates to novel methods and bacteria for the increased dinitrogen ($N_2$) fixation of nodulating leguminous plants. More specifically, the present invention is directed to herbicide resistant $N_2$ fixing bacteria, which have been isolated through selection of mutants or resistant variants or genetically engineered for herbicide resistance, and to nodulating leguminous plants infected with the herbicide resistant $N_2$ fixing bacteria. The present invention is also directed to methods to enhance $N_2$ fixation, nodulation, growth and/or grain yield of leguminous herbicide resistant or tolerant plants treated with the herbicide. The present invention is especially useful for increasing competitiveness of superior dinitrogen fixing strains over indigenous strains which are not resistant, under field conditions. Leguminous plants or seeds which are treated with a herbicide of interest are inoculated with the novel herbicide resistant rhizobia, preferably by applying the bacteria to the seeds or introducing the bacteria into the seed furrows at the time of planting, such that the novel rhizobia are able to form a symbiotic relationship with the plant.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Leguminous plants, such as soybean (*Glycine max* [L.] Merrill), form a symbiotic relationship with $N_2$ fixing bacteria that allows the association of the two organisms to reduce ("fix") dinitrogen gas in the atmosphere into a form which the plants can use as a nitrogen source. As a result, the plants do not require extensive nitrogen fertilization. The bacteria forming symbioses with legumes belong to the family Rhizobiaceae, which are a diverse group of gram-negative, nonspore-forming, rod-shaped, aerobic bacteria belonging to Group IV bacteria (Holt et al., 1994). Originally, rhizobia were classified as a single genus. More recent classifications, however, have divided rhizobia into distinct taxonomic groups based upon sequence similarities of 16s rRNA (Crawford et al., 2000). Current taxonomic divisions of rhizobia have grouped several clusters of rhizobia together within the alpha-proteobacteria based upon these sequence similarities. Among the most common genera within rhizobia are: *Rhizobium, Sinorhizobium, Azorhizobium, Mesorhizobium*, and *Bradyrhizobium*. The ability of a rhizobia to nodulate its host exhibits specificity. For example, rhizobia which form symbiotic, $N_2$ fixing nodules generally belong to one of many strains within rhizobia, including *B. japonicum* subspecies 1 and 2, *B. elkanii* and *S. fredii* (Devine and Kuykendall, 1996). The *B. elkanii* strains share a DNA homology and generally nodulate cowpea (*Vigna unguiculata*) as well as soybean. The *B. elkanii* strains can cause rhizobitoxine-induced chlorosis (Erdman et al., 1957). Some soybean plants can also enter symbiotic relationships with a fast-growing rhizobia species, *Sinorhizobium fredii*.

The bacteria infect the root, forming a nodule where biological $N_2$ fixation occurs that supplies 40 to 85% of the soybean's nitrogen requirements (Graham, 1998). Nitrogen fixation commences about three weeks after the infection process begins and is indicated by large, irregularly shaped nodules having a beef-steak red interior color due to the presence of leghemoglobin. Early in the growing season, nodules are clustered near the root crown. Later, the nodules located on secondary roots become more important in $N_2$ fixation activity. Nodules must be present for $N_2$ fixation to occur. However, not all nodules are effective. Effectiveness of nodules is reflected in the ability of the nodules to fix dinitrogen. Effective nodules are those nodules formed on legume roots that have the ability to fix (reduce) $N_2$ symbiotically at high rates relative to a recognized superior rhizobial strain which serves as a standard, such as strain USDA 110 for *B. japonicum* infecting soybean. Rates of $N_2$ fixation may be determined directly by quantifying the amount of $^{15}N$-labeled organic nitrogen per unit time per unit nodule mass following exposure of nodules to $^{15}N_2$ for a set period of time. Alternatively, effective nodules may be determined indirectly by quantifying the conversion rate of acetylene to ethylene by nodules formed by a specific rhizobial strain relative to that of a recognized superior rhizobial strain which serves as a standard, such as strain USDA 110 for *B. japonicum*. The rate of acetylene reduction is measured by standard methods (Purcell et al., 1997; King et al., 2001) of flowing 1:9 acetylene:air mixture at a constant and known flow rate through a sealed pot having an inlet and exit port and containing the nodulated roots of said legume. Gas samples are taken from the effluent stream with a syringe when the quotient of the pot volume to volumetric flow rate is four. Gas samples are injected into a gas chromatograph with a flame ionization detector for ethylene determination. Various screening studies indicate that, of the nodules on a typical soybean plant, approximately 25% are highly effective, 50% are of medium effectiveness, and 25% are ineffective. Thus, the number of nodules on the soybean root is not the only indicator of adequate $N_2$ fixing ability.

Glyphosate [N-(phosphonomethyl)glycine] is the active ingredient in the non-selective herbicide Roundup™ (Monsanto Co., St. Louis, Mo. 63167). Advances in biotechnology have resulted in glyphosate resistant or tolerant (GR) soybean cultivars, providing an effective broad-spectrum postemergence weed-control option. Glyphosate competitively inhibits 5-enolpyruvylshikimate-3-phosphate synthase (EPSPS) (E.C. 2.5.1.19), an enzyme in the shikimate pathway leading to the synthesis of aromatic amino acids (Duke, 1988). Commercial glyphosate resistant or tolerant (GR) soybean expresses an EPSPS that is resistant or tolerant to glyphosate. The gene for resistance was originally isolated from *Agrobacterium* sp. (Padgette et al., 1995). Extensive research on the effects of glyphosate on soybean in relatively high yield environments (2000 to 4000 kg ha$^{-1}$) has indicated that there is no effect of glyphosate relative to untreated plants under weed free conditions (Delannay et al., 1995).

Glyphosate is not readily degraded in soybean and concentrates in metabolic sinks, such as young roots and developing and mature nodules (Duke, 1988). Previous research indicates that a single foliar application of glyphosate at 0.5 kg ha$^{-1}$ can result in concentrations up to 0.3 mM in bulk root tissue of susceptible plant species (Honegger et al., 1986). Higher glyphosate use rates or repeated applications could result in even greater concentrations, especially in the stronger metabolic sinks such as soybean root nodules as compared to the bulk root system (McWhorter et al., 1980).

Symbiotic $N_2$ fixation is critical for obtaining high yields in soybean grown on soils without large amounts of available nitrogen (Cooper and Jeffers, 1984). Importantly, $N_2$ fixation in soybean is more sensitive to water-deficit stress than are other processes such as gas exchange (Durand et al., 1987), transpiration (Sall and Sinclair, 1991), and uptake and assimilation of inorganic soil nitrogen (Purcell and King, 1996).

Although EPSPS in GR soybean is resistant or tolerant to glyphosate, strains of the $N_2$ fixing symbiont such as *Bradyrhizobium japonicum* have a sensitive form of the enzyme (Jaworski, 1972; Moorman et al., 1992). The sensitivity of *B. japonicum* to glyphosate is influenced by herbicide concentration and bacterial strain. Growth of *B. japonicum* strain, USDA 110, in culture has been inhibited 41 to 100% at glyphosate concentrations of 0.5 to 5 mM (Moorman et al., 1992). Strains USDA 123 and 138 are less sensitive at 0.5 to 1 mM glyphosate, with inhibition of only 10 to 20%, however, they are inhibited 100% at a 5 mM concentration. *B. japonicum* strain USDA 71 is very sensitive, with bacterial growth decreased 69 to 92% by glyphosate concentrations of 0.01 to 1 mM (Jaworski, 1972). Despite recognition of *B. japonicum* sensitivity to glyphosate, there have been no previous reports of the effect of glyphosate on $N_2$ fixation, nodulation or biomass in GR soybean in symbiosis with rhizobia species.

Superior dinitrogen fixing strains have been selected and used to infect leguminous plants in an attempt to increase $N_2$ fixation. While these strains have demonstrated increased $N_2$ fixation in controlled environments, they have not been effective in field environments where the indigenous bacterial populations have out-competed them for sites on legume roots. Thus, there is a definite need for a method to increase competitiveness of superior nitrogen fixing strain against indigenous populations. The present invention solves this need as illustrated herein.

SUMMARY OF THE INVENTION

The present invention is directed to herbicide resistant $N_2$ fixing rhizobia and to a method for enhancing $N_2$ fixation by the herbicide resistant rhizobia in symbiosis with herbicide resistant or tolerant leguminous plants treated with herbicide. The present invention is especially useful for enhancing competitiveness of over indigenous soil rhizobia which are not resistant. Briefly, the invention is directed to selected or engineered herbicide resistant rhizobia. The resistant rhizobia are used as an inoculant for leguminous plants resistant or tolerant to the herbicide. The presence of the resistant rhizobia under field conditions enhances nodulation of the resistant or tolerant leguminous plants treated with herbicide compared to nodulation by indigenous strains of rhizobia which are not resistant.

BRIEF DESCRIPTION OF THE FIGURES

FIGS. 5A and C show results from a greenhouse experiment in which separate harvests were made at 10 and 17 days after planning (DAP). FIGS. 5B and D show results from a growth chamber experiment in which a single harvest was made at 15 DAP.

DETAILED DESCRIPTION OF THE INVENTION

Figure 1:
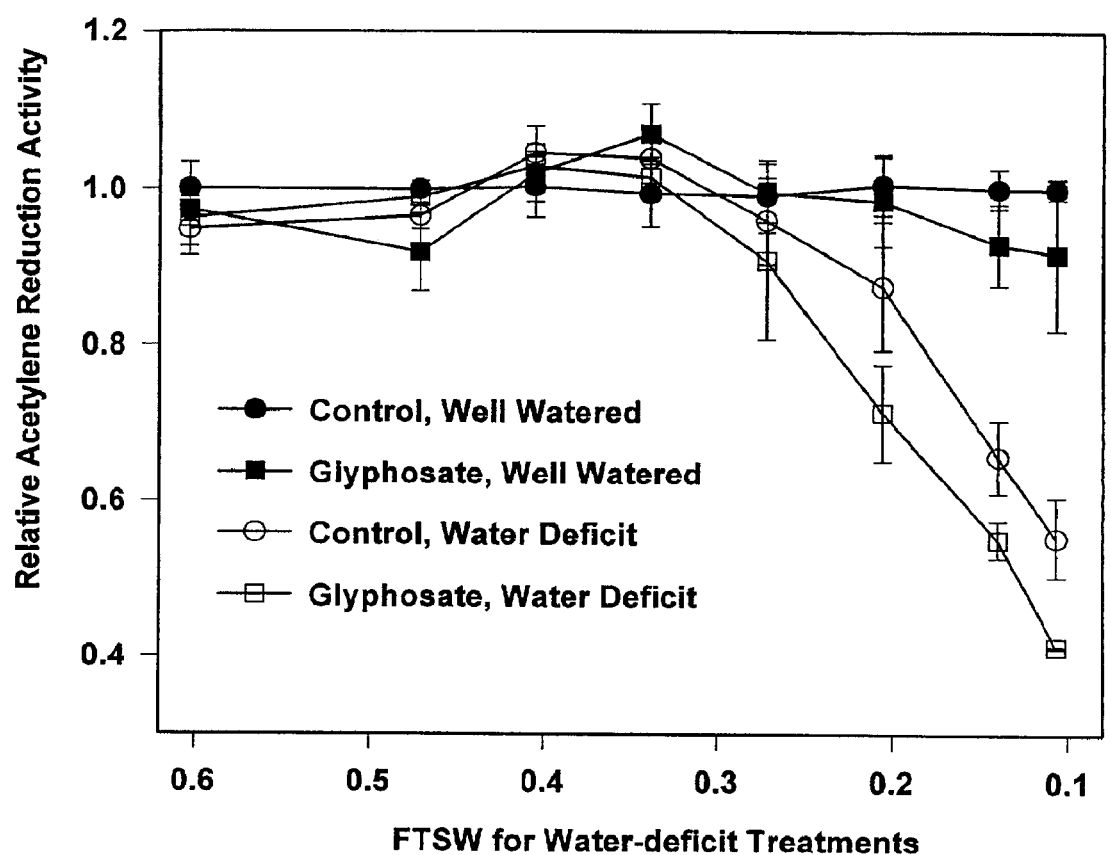
FIG. 1 shows relative acetylene reduction activity (ARA) of TV5866RR soybean in the growth chamber in response to glyphosate treatment under well-watered and water-deficit conditions. Glyphosate was applied at 1.68 kg ha$^{-1}$ at 5, 12, and 19 days after emergence for the glyphosate-treated plants. Well-watered plants were maintained at a fraction of transpirable soil water (FTSW) of 0.6, and water-deficit plants were watered daily to the indicated FTSW during the drying cycle. Values are the mean±SE (n=7).

The present invention is directed to herbicide resistant $N_2$ fixing rhizobia and a method of use for enhancing $N_2$ fixation, nodulation, growth grain yield and/or competitiveness of improved rhizobial strains in symbiosis with resistant or tolerant leguminous plants treated with the herbicide. Accordingly, one aspect of the present invention is a novel herbicide resistant, $N_2$ fixing rhizobia. In one embodiment of this aspect, the novel rhizobia is an $N_2$ fixing species genetically engineered for herbicide resistance. In another embodiment of this aspect, the novel rhizobia is isolated through selection pressure of variants from within existing $N_2$ fixing species. In a further embodiment, the novel rhizobia is selected as an induced mutant of non-herbicide resistant $N_2$ fixing species. More particularly, the present invention relates to rhizobia species which are resistant to 5-enolpyruvylshikimate-3-phosphate synthase (EPSPS) inhibitors and are capable of nodulating leguminous plants after application of herbicide which inhibits EPSPS, such as glyphosate.

In another aspect of the present invention, herbicide resistance is obtained in superior $N_2$ fixing strains of rhizobia. Examples of superior $N_2$ fixing strains include *Bradyrhizobium* sp. of Vasilas and Fuhrmann (1993); Fuhrmann and Vasilas (1993); U.S. Pat. Nos. 5,021,076; 5,045,461; 5,308,616; 4,863,866; and 4,720,461.

It has been found that glyphosate impacts the symbiotic relationship between GR soybean cultivars and non resistant legume nodulating rhizobia. As one example of the present invention, it has been discovered that the novel bacteria of the present invention, in symbiosis with GR soybean plants, enhanced $N_2$ fixation of plants treated with glyphosate. The present invention has been demonstrated with reference to glyphosate resistant *B. japonicum* in symbiosis with GR soybean plants transformed with the glyphosate resistant or tolerant EPSPS gene derived from *Agrobacterium* spp. strain CP4. However, *B. japonicum* is representative and not limiting and the invention can also be practiced with other rhizobial species. One skilled in the art would recognize that the present invention can also be practiced with the use of other nucleotide sequences having a substantially similar function of providing an enzyme with resistance to inhibition by glyphosate, such as a mutated aroA gene (U.S. Pat.

No. 5,094,945; 4,769,061), or with other nucleotide sequences isolated from an $N_2$ fixing bacterium selected for the resistance to an herbicide of interest. Likewise, leguminous crops other than soybean may be used in the practice of the invention (U.S. Pat. No. 5,922,316). Table 1 lists alternative rhizobia and their leguminous hosts which can be used in the practice of the method of the present invention (Crawford et al., 2000).

| BACTERIAL SPECIES | HOST PLANTS (GENUS) |
| --- | --- |
| Sinorhizobium meliloti | Medicago (alfalfa), Melilotus (sweetclover) |
| S. fredii | Glycine (soybean), Vigna (cowpea) |
| Sinorhizobium sp. NGR234 | Broad host range across many genera: Vigna, Leucanena, Macroptilium (siratro) |
| Rhizobium leguminosarum biovar viciae | Vicia (vetch), Pisium (pea), Cicer (chickpea), Lathyrus (sweet pea) |
| R. leguminosarum biovar trifolii | Trifolium (clover) |
| R. leguminosarum biovar phaseoli | Phaseolus (bean) |
| R. tropici | Phaseolus, Leucaena, Medicago |
| R. etli | Phaseolus |
| Mesorhizobium loti | Lotus (trefoil) |
| Bradyrhizobium japonicum | Glycine |
| B. elkani | Glycine, Vigna |
| Azorhizobium caulinodans | Sesbania rostrata |

Furthermore, resistance to other herbicides which inhibit EPSPS as well as other herbicides, such as glufosinate, are contemplated within the scope of the present invention. Glufosinate is a glutamine sythetase inhibitor, used as an active ingredient in herbicide for application to soybean and other leguminous plants (U.S. Pat. No. 6,040,270). Transgenic soybean plants have been engineered which have resistance to glufosinate (U.S. Pat. No. 5,998,700).

Definitions

In the description that follows, a number of words are used extensively. The following definitions are provided to facilitate understanding of the invention.

"DAE" refers to the number of days after emergence.

"EPSPS" refers to 5-enolpyruvylshikimate-3-phosphate synthase (EC: 2.5.1.19)

"Early application" refers to application at or prior to the V3 developmental stage as defined by Fehr and Caviness, 1977.

"Effective nodules" are those nodules formed on legume roots that have the ability to fix (reduce) $N_2$ symbiotically at high rates relative to a recognized superior rhizobial strain which serves as a standard, such as strain USDA 110 for B. japonicum infecting soybean. Rates of $N_2$ fixation may be determined directly by quantifying the amount of $^{15}N$-labeled organic nitrogen per unit time per unit nodule mass following exposure of nodules to $^{15}N_2$ for a set period of time. Alternatively, effective nodules may be determined indirectly by quantifying the conversion rate of acetylene to ethylene by nodules formed by a specific rhizobial strain relative to that of a recognized superior rhizobial strain which serves as a standard, such as strain USDA 110 for B. japonicum. The rate of acetylene reduction is measured by standard methods (Purcell et al., 1997; King et al., 2001) of flowing 1:9 acetylene:air mixture at a constant and known flow rate through a sealed pot having an inlet and exit port and containing the nodulated roots of said legume. Gas samples are taken from the effluent stream with a syringe when the quotient of the pot volume to volumetric flow rate is four. Gas samples are injected into a gas chromatograph with a flame ionization detector for ethylene determination.

"Encode" refers to a polynucleotide said to "encode" a polypeptide if, in its native state or when manipulated by methods well known to those skilled in the art, it can be transcribed and/or translated to produce the RNA for and/or the polypeptide or a fragment thereof. The anti-sense strand is the complement of such a nucleic acid and the encoding sequence can be deduced therefrom.

"Enhanced modulation of a nodulating leguminous plant" refers generally to the increase in the number of nodules formed and/or fraction of the total nodule mass on the roots of the plant after the roots of the plant are infected, which result in the formation of effective nodules.

"Enhanced (or Enhancing) competitiveness" of a particular rhizobia refers to increasing the ability of a specific rhizobial strain to infect (enter) the leguminous plant root and form effective nodules relative to other rhizobial strains.

"Enhancing growth of a leguminous plant" refers to a greater increase in plant mass/unit time, and/or increase in seed yield, and/or increase in rate of plant growth.

"Enhanced (or Enhancing) dinitrogen fixation of a modulating leguminous plant" refers to an increased amount of nitrogen accumulation/unit time/plant, and/or an increased amount of acetylene gas reduced to ethylene/unit time/plant as a result of enhanced nodulation.

"Glyphosate resistance" and "Glyphosate resistant" when referring to nitrogen fixing rhizobia of the present invention refers to the ability of the bacteria to survive and reproduce following exposure to a dose of glyphosate normally lethal to a non-resistant rhizobia wild type.

"Herbicide resistance" refers to the inherited ability of a bacteria or plant to survive and reproduce following exposure to a dose of herbicide normally lethal to the wild type. Resistance may be naturally occurring or induced by such techniques as genetic engineering or selection of variants produced by tissue culture or mutagenesis (Weed Sci. 46:628–630, 1998, incorporated herein by reference).

"Herbicide tolerance" refers to the inherent ability of a species to survive and reproduce after herbicide treatment. This implies that there was no selection or genetic manipulation to make the species tolerant; it is naturally tolerant (Weed. Sci. 46:628–630, 1998, incorporated herein by reference).

"Inoculate" and "Inoculating" when referring to the rhizobia and leguminous plants of the present invention refer to the introduction of viable rhizobia into seed furrows at time of planting or applying the rhizobia to the seeds at a population sufficient to form effective nodules.

"Nondestructive" refers to the ability of quantitating acetylene reduction activity without killing or detrimentally affecting the seed, plant or rendering the nodule or enzyme non-enzymatically active.

"Operably linked" refers to a juxtaposition wherein the components so described are in a relationship permitting them to function in their intended manner, i.e., a promoter is operably linked to a coding sequence if the promoter affects its transcription or expression.

"Recombinant nucleic acid" refers to a nucleic acid which is not naturally occurring, or which is made by the artificial combination of two otherwise separated segments of sequence. This artifice combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory control" refers in general to the modulation of gene expression induced by DNA sequence elements, particularly those located upstream of (5' to) the transcription start site. Regulation may be analogous to an on/off switch which responds to environmental conditions or regulation may result in variations in the level of gene expression or its tissue specificity. Placing a structural gene under the regulatory control of a promoter or a regulatory sequence element means positioning the structural gene such that the expression of the gene is controlled by these sequences, i.e., operably linked. Promoters are generally positioned 5' (upstream) to the genes that they control. In the construction of heterologous promoter/structural gene combinations, it is generally preferred to position the promoter at a distance from the gene transcription start site that is approximately the same as the distance between the promoter and the gene it controls in its natural setting, i.e., the gene from which the promoter is derived. As is known in the art, some variation in this distance can be accommodated without loss of promoter function.

"Rhizobia" refers to members of genera *Rhizobium, Sinorhizobium, Azorhizobium, Mesorhizobium*, and *Bradyrhizobium* that form symbiotic relationships with leguminous plants, including *B. japonicum, Bradyrhizobium elkanii, Sinorhizobium fredii, Sinorhizobium meliloti, Sinorhizobium* sp. NGR234, *Rhizobium leguminosarum* biovar *viciae, R. leguminosarum* biovar *trifolii, R. leguminosarum* biovar *phaseoli, R. tropici, R. etli, Mesorhizobium loti, B. elkani* and *Azorhizobium caulinodans* (Crawford et al., 2000).

"Substantial homology or similarity"—A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least doubt 14 nucleotide, preferably at least about 65%, more preferably at least about 75% and most preferably at least about 90%. See, Kanehisa, 1984. The length of homology comparison, as described, may be over longer stretches, and in certain embodiments will often be over a stretch of at least about nine nucleotide, usually at least about 20 nucleotide, more usually at least about 24 nucleotide, typically at least about 28 nucleotide, more typically at least about 32 nucleotide, and preferably at least about 36 or more nucleotide.

Nucleic acid hybridization will be affected by such conditions as salt concentration, temperature or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30 C, typically in excess of 37 C, and preferably in excess of 45 C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid and can be determined by techniques well known in the art. See, e.g., Wetmur and Davidson, 1968.

A "structural gene" is that portion of a gene comprising a DNA segment encoding a protein, polypeptide or a portion thereof. The term can refer to copies of a structural gene naturally found within the cell, but artificially introduced, or the structural gene may encode a protein not normally found in the cell into which the gene is introduced, in which case it may be referred to as a heterologous gene.

"Substantially similar function" refers to the function of a modified nucleic acid with reference to the original nucleic acid The modified nucleic acid is prepared by conventional techniques and includes nucleic acids with a function substantially similar to the original gene.

"Superior dinitrogen fixing strain" refers to rhizobial strains which demonstrate increased $N_2$ fixation under controlled or field environments, as compared to indigenous strains which are not resistant.

"Symbiotic nitrogen fixation" refers to the chemical reduction of dinitrogen gas ($N_2$) to ammonia ($NH_3$) and subsequent assimilation to amines, amides, ureides, and other nitrogen-containing compounds which are formed in nodules formed by the symbiotic association of a legume and the rhizobia species infecting the nodule.

Soybean growth stages are defined using the conventional designation of Fehr and Caviness (Spec. Report No. 80, Iowa State Univ. Coop. Ext. Ser., Ames, Iowa (1977)) whereby: V1 refers to plants during vegetative growth with one fully developed leaf at the unifoliolate node; V2 refers to plants during vegetative growth with one fully developed trifoliolate leaf at the node above the unifoliolate node; V3 refers to plants during vegetative growth with three nodes on the main stem with fully developed leaves beginning with the unifoliolate node; Vn refers to plants during vegetative growth with "n" nodes on the main stem with fully developed leaves beginning with the unifoliolate node; R1 refers to plants during reproductive growth with one open flower at any node on the main stem; R2 refers to plants during reproductive growth with an open flower at one of the two uppermost nodes on the main stem with a fully developed leaf; R5 refers to plants with seed 2 mm in length in a pod at one of the four uppermost nodes on the main stem with a fully developed leaf; R6 refers to plants during reproductive growth with a pod with a green seed that fills the pod cavity at one of the four uppermost nodes on the main stem with a fully developed leaf; R7 refers to plants during reproductive growth that have one normal pod on the main stem that has reached its mature pod color.

Through the treatment of commercially available GR soybean with glyphosate at several different stages of development and the subsequent evaluation of $N_2$ fixation, growth, and yield in a series of greenhouse, growth chamber, and field experiments, it has been discovered that glyphosate impacts the symbiotic relationship that results in $N_2$ fixation in soybean. The invention is emplified by glyphosate-treated GR soybean varieties. However, it will be appreciated by a skilled practitioner that it may be applicable to other leguminous plants and to treatment with other herbicides, as discussed above.

It has been found that early applications of glyphosate delayed $N_2$ fixation and decreased biomass and nitrogen accumulation in the cultivar TV5866RR harvested at 19 days after emergence (DAE) (King et al., 2001, *Agron. J.* 93:179–186, incorporated herein). However, plants had recovered by 40 DAE. The delay in $N_2$ fixation in the growth chamber experiments and decreased nitrogen accumulation in greenhouse experiments described herein are consistent with disruption of normal nodulation. Roots continue to form nodules until the plant has an adequate supply of nitrogen, which apparently inhibits further nodule initiation (Parsons et al., 1993). In infected cells of a nodule, *B. japonicum* are enclosed within the symbiosome membrane, which in mature nodules is highly selective and separates the bacteria from the cytosol (Udvardi and Day, 1997). However, in early stages of nodule development, the symbiosome membrane may not selectively restrict glyphosate movement. In this regard, it may be relevant that cell division of cultured *B. japonicum* has been demonstrated to be restricted in the presence of glyphosate (Jaworski, 1972). While not wanting to be bound by a particular mode of action, this could explain the delay in $N_2$ fixation for glyphosate-treated plants.

It has been unexpectedly discovered, as illustrated herein, that conditions which adversely affect the symbiotic relationship between soybean and *B. japonicum*, such as glyphosate in the soybean root system, also influence the sensitivity of $N_2$ fixation to water deficits. For example, in growth chamber studies, $N_2$ fixation was found to be more sensitive to water deficits in glyphosate-treated plants. In field studies, there were no observable effects of glyphosate on glyphosate resistant or tolerant (GR) soybean where there is adequate soil water throughout the growing season. However, under conditions of limited soil water, glyphosate tends to decrease biomass and seed yields. This response of glyphosate-treated, GR soybean to water-deficit conditions was unexpected and has not been previously reported.

Under well-watered conditions, the delay in active $N_2$ fixation had no or little long-term impact on biomass and nitrogen accumulation. For example, there was no difference in total biomass or nitrogen content between glyphosate-treated and untreated plants at 40 days after emergence (DAE) following two applications of glyphosate in greenhouse studies. This response is consistent with results from field experiments where there is adequate soil water. Previous field studies comparing GR cultivars, treated and untreated with glyphosate under weed-free conditions, reported no yield decrease to glyphosate under relatively high-yielding conditions (Delannay et al., 1995).

Early studies (Jaworski, 1972; Moorman et al., 1992) reported that growth of *B. japonicum* in culture is inhibited by glyphosate at concentrations predicted to be present in roots and nodules of glyphosate-treated plants (Honegger et al., 1986; McWhorter et al., 1980). It has been unexpectedly discovered that applications of glyphosate to young soybean delays $N_2$ fixation and increases the sensitivity of $N_2$ fixation to water deficits. Although the invention is exemplified by the symbiotic relationship between herbicide resistant *B. japonicum* and soybean cultivars, it is applicable to symbioses that form between other rhizobial and leguminous species (Table 1). As those of ordinary skill in the art will recognize, Table 1 only provides a partial list of rhizobial and leguminous species that can be employed in the method of the present invention. Furthermore, as those of skill in the art will recognize, other genes that confer resistance to an herbicide may also be used to genetically engineer resistant rhizobia. Exemplary are:

(a) A herbicide that inhibits the growing point or meristem of a plant, such as an imidazalinone or a sulfonylurea. Exemplary genes in this category code for mutant ALS (Lee et al., 1988) and AHAS enzyme (Miki et al., 1990).

(b) Glyphosate (resistance imparted by mutant EPSP synthase and araA genes) and other phosphono compounds such as glufosinate (PAT and bar genes), and pyridinoxy or phenoxy proprionic acids and cyclohexones (ACCase inhibitor encoding genes). See, for example, U.S. Pat. No. 4,940,835, which discloses the nucleotide sequence of a form of EPSP synthase which can confer glyphosate resistance. A DNA molecule encoding a mutant aroA gene can be obtained under ATCC accession number 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthase genes which confer resistance to herbicides such as L-phosphinothricin. The nucleotide sequence of a phosphinothricin acetyltransferase gene is provided in European application No. 0 242 246. DeGreef et al. (1989) describes the production of transgenic plants that express chimeric bar genes coding for phosphinothricin acetyltransferase activity. Exemplary of genes conferring resistance to phenoxy proprionic acids and cyclohexones, such as sethoxydim and haloxyfop, are the Acc1-S1, Acc1-S2 and Acc1-S3 genes described by Marshall et al. (1992).

(c) A herbicide that inhibits photosynthesis, such as a triazine (psbA and GST genes) and a benzonitrile (nitrilase gene). Przibilla et al. (1991) describes the use of plasmids encoding mutant psbA genes to transform *Chlamydomonas*. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a GST (glutathione S-transferase) is described by Hayes et al. (1992).

(d) A herbicide having dinitroaniline as an active ingredient, such as Trifuralin and Pendimethalin. Trifuralin decreases nodulation and $N_2$ fixation in soybean (Baltazar and Brotonegoro, 1980.

In addition to the delay in $N_2$ fixation and increased sensitivity of $N_2$ fixation to water deficits by glyphosate treatment, it has also been discovered that soybean root growth is inhibited by repeated applications of glyphosate under greenhouse growth conditions. Biomass and nitrogen content of GR soybean were also decreased by glyphosate in plants grown with available soil nitrogen. The data presented herein identifies differences in sensitivity to glyphosate among GR cultivars, with biomass decreases in response to glyphosate ranging from 0 to 30% at 40 DAE for the most resistant and sensitive cultivars, respectively.

Method of Use:

Increased Competitiveness of Superior Dinitrogen fixing Rhizobial Strains.

Attempts to improve legume productivity in agricultural fields by inoculation with superior strains of rhizobia often fail. This failure is the result of the inability of the superior inoculum strains to occupy nodules in soils with a large population of indigenous rhizobia. For example, Weaver and Frederick (1974) found that inoculation with a strain at a level 1,000 times higher than the number of *Bradyrhizobia* in the soil resulted in one-half of the nodules being occupied by the inoculum strain.

The need to solve the competition problem has increased because of successful efforts to identify genes in rhizobial strains that increase symbiotic nitrogen fixation rates and/or improve legume yield under controlled conditions. Genes coding for improved nitrogenase activity and/or legume productivity have been described (Cannon et al., 1988; Spaink et al., 1989). This increase occurs when the expression of such genes is increased or modified and when the plants are grown under controlled conditions. Such genes include the following: (1) nifA, appositive regulator of the nitrogen fixation genes; (2) dct, the operon responsible for dicarboxylic acid transport; and (3) nodD, a regulatory gene required for the expression of the nod genes in rhizobia. There are also reports in the literature of the use of chemical mutagenesis to generate mutants of rhizobia with increased symbiotic nitrogenase activities compared to the wild-type strains.

Nitrogen fixation occurs in soils with depleted nitrogen content following the infection of legume roots with nitrogen fixing bacteria and the establishment of a symbiotic relationship. Therefore, herbicide resistant rhizobial strains can overcome the inhibition caused by the herbicide. Furthermore, by providing herbicide resistance to superior dinitrogen fixing strains, more nitrogen would be available to the plant, thereby increasing plant growth, productivity and grain yield. Thus, the method of the present invention can be employed to increase the competitiveness of desired herbicide resistant rhizobial strains over undesired indigenous strains, which are not resistant to the herbicide, in symbiosis with resistant or tolerant host plants which do not metabolize the herbicide of interest.

The practice of the present invention employs, unless otherwise indicated, conventional techniques of chemistry, molecular biology, microbiology, recombinant DNA, genetics, immunology, and introduction of DNA into bacteria. See, e.g., Maniatis et a., 1982; Sambrook et al., 1989; Ausubel et al., 1992; Glover, 1985; Anand, 1992; Guthrie and Fink, 1991, which are expressly herein incorporated by reference.

EXAMPLES

The present invention is further detailed in the following Examples, which are offered by way of illustration and are not intended to limit the invention in any manner. Standard techniques well known in the art or the technique specifically described below are utilized.

Example 1

Postemergence Application of Glyphosate to Glyphosate Resistant Soybean Decreases Nitrogen Fixation A. Under Greenhouse Cultivation.

Experiments were conducted to evaluate growth of the GR soybean cultivar Terral TV5866RR (TV5866RR) in response to postemergence glyphosate applications. Seeds were planted in 15-cm pots with an approximate soil volume of 1.9 L. The potting medium was a nitrogen-free peat/vermiculite/perlite mixture (LB2, Sun Gro Horticulture Inc., 1830 Knob Hill, Garland, Tex. 75403). Soil was saturated with deionized (DI) water and then 500 mL of full-strength, nitrogen-free nutrient solution (de Silva et al., 1996) was added prior to planting. Pots were inoculated with approximately $1 \times 10^7$ cells of B. japonicum (USDA 110) at sowing. After emergence, plants were thinned to one per pot and reinoculated with B. japonicum. Plants were well watered by adding deionized (DI) water daily, and each pot received 250 mL of nitrogen-free nutrients weekly after emergence. Day and night temperatures were approximately 30 and 24 C, respectively, and natural illumination was supplemented with 1000 W metal-halide lamps for a day length of 16 h.

Glyphosate (Roundup Ultra Herbicide®, Monsanto Co., St. Louis, Mo. 63167) was applied at 1.68 kg a.i. $ha^{-1}$ in a carrier volume of 93 L $ha^{-1}$ and at a spray pressure of 260 kPa. Each application was as a postemergence over-the-top spray to soybean plants using a moving-nozzle spray chamber. Herbicide application and harvest schedules are given in Table 2. At each harvest, plants were separated into shoots, roots, and nodules. Nodules were photocopied, and total number of nodules per plant was determined from the photocopies. Plant sections were oven dried at 65 C for 48 h, weighed, and ground to pass a 1-mm sieve. Total nitrogen was determined for shoots and root plus nodule dry matter with a Leco FP-228 Determinator (Leco Corporation, St Joseph, Mich.) by the Agriculture Services Laboratory, University of Arkansas. The experiment consisted of six replications and was repeated. Seed for Run 1 and Run 2 of the experiment were planted on 25 February and 14 April, respectively. Biomass, total nitrogen, and nodule data were analyzed by harvest using analysis of variance with glyphosate treatment as a fixed effect and replication as a random effect. Treatment means were compared using Fisher's Protected least significant difference (LSD, $P \leq 0.05$).

TABLE 2

Glyphosate treatments applied to TV5866RR in Greenhouse Example 1.

| | | Application timing† | |
|---|---|---|---|
| Treatment | Harvest§ | DAE‡ | Growth stage‡ |
| none | 1§ | — | — |
| early | 1 | 5, 10 | V1, V2 |
| none | 2 | — | — |
| early | 2 | 5, 10 | V1, V2 |
| late | 2 | 18, 25, 32 | V4, V5, V7 |

†Each glyphosate application was at 1.68 kg $ha^{-1}$.
‡DAE, days after emergence.
§Soybean growth stages at each application timing.
§Harvest 1 and 2 were at 19 and 40 DAE, respectively.

Glyphosate affected biomass and nitrogen accumulation of TV5866RR at Harvest 1 (19 DAE) in Runs 1 and 2 (Table 3). Shoot biomass was decreased 17%, but root biomass was not decreased by glyphosate at Harvest 1. Nitrogen accumulation was decreased 36% and 34% in roots and shoots, respectively, of glyphosate-treated plants at Harvest 1 (19 DAE) averaged across runs. There was no difference in the number of nodules per plant, but total nodule weight was decreased 34% in Run 1 of the experiment. In Harvest 1, Run 2, however, nodule mass was not affected at 19 DAE.

TABLE 3

Biomass and nitrogen content of TV5866RR in response to glyphosate at Harvest 1 (19 DAE) in Greenhouse Example 1.

| | Biomass | | | | Nitrogen | |
|---|---|---|---|---|---|---|
| Glyphosate | | Shoot | Nodules | | | |
| treatment | Root | Run 1 | Run 2 | | Root | Shoot |
| | g $plant^{-1}$ | | | | mg $plant^{-1}$ | |
| none | 0.19 | 0.48 | 0.065 | 0.085 | 6.4 | 14.0 |
| early† | 0.17 | 0.40 | 0.043 | 0.088 | 4.2 | 8.9 |

TABLE 3-continued

Biomass and nitrogen content of TV5866RR in response to
glyphosate at Harvest 1 (19 DAE) in Greenhouse Example 1.

| Glyphosate treatment | Biomass | | | Nitrogen | |
|---|---|---|---|---|---|
| | Root | Shoot Run 1 | Nodules Run 2 | Root | Shoot |
| LSD (0.05)‡ | NS | 0.07 | — | 1.5 | 5.0 |
| within a run§ | — | | 0.016 | — | |
| between runs | — | | 0.017 | — | |

†Early treatment consisted of glyphosate applied foliarly at 1.68 kg h$^{-1}$ 5 and 12 DAE.
‡Main effect of the treatment was significant for shoot biomass. Root biomass was not affected by glyphosate treatment at Harvest 1.
§There was a significant run by treatment interaction for nodule biomass.

Visual observations were consistent with a greater effect of glyphosate on nitrogen accumulation and $N_2$ fixation than on biomass accumulation at 19 DAE. Plants treated with glyphosate yellowed between 12 and 20 DAE. The decrease in individual nodule size is indicative of less effective nodules (Singleton and Stockinger, 1983).

By Harvest 2, at 40 DAE, the only evident effect of glyphosate was on soybean nodules (Table 4). In Harvest 2, Run 1, the untreated plants had fewer nodules that were larger than nodules of glyphosate-treated plants. The increased number of nodules for glyphosate-treated plants offset the decrease in individual nodule size, resulting in similar total nodule mass among treatments. Glyphosate had no apparent effect on soybean plants by 40 DAE in Run 2 with regards to plant mass, plant color, or plant N content (Table 4). Although greenhouse temperature and day length were similar between runs of the experiment, there were probably differences in light intensity associated with the February and April planting dates for Runs 1 and 2, respectively. This could account for differences in response to glyphosate between Run 1 and Run 2 for total nodule mass at Harvest 1 and for individual nodule mass at Harvest 2.

TABLE 4

TV5866RR root nodule response to glyphosate at Harvest 2
(40 DAE) in Greenhouse Example 1.

| Glyphosate treatment† | Individual nodule mass | | Nodules per plant | | Total nodule mass | |
|---|---|---|---|---|---|---|
| | Run 1 | Run 2 | Run 1 | Run 2 | Run 1 | Run 2 |
| | mg nodule$^{-1}$ | | number | | g plant$^{-1}$ | |
| None | 3.57 | 1.76 | 111 | 226 | 396 | 398 |
| Early | 2.73 | 1.70 | 138 | 256 | 377 | 435 |
| Late | 2.79 | 2.00 | 150 | 209 | 418 | 418 |
| LSD (0.05)‡ | — | — | 23 | NS | — | — |
| within a run§ | 0.36 | | — | | NS | |
| between runs | 0.60 | | — | | NS | |

†Glyphosate was applied at 1.68 kg ha$^{-1}$ on 5 and 12 DAE for the early treatment and 18, 25, and 32 DAE for the late treatment.
‡Number of nodules per plant was analyzed by experiment because of a lack of homogeneity of variance between experiments.
§There was a significant run by glyphosate treatment interaction for individual nodule mass and no significant difference among treatments for total nodule mass.

B. Under Growth Cabinet Cultivation.

The time course of nodule activity from 14 to 28 DAE was followed in a series of four runs of an experiment in a growth cabinet. Soybean seeds were sown in N-free potting media in pots constructed of 15-cm diameter polyvinyl chloride pipe. These pipes allow nondestructive measurement of nodule activity by the acetylene reduction assay as described by Purcell et al. (1997). Seeds were inoculated with *B. japonicum* (USDA 110), and pots were supplied with N-free nutrients. One-half of the plants were sprayed with glyphosate as described in Example 1.A. at 5, 12, and 19 DAE. Acetylene reduction activity (ARA) was measured at 14, 21, and 28 DAE by passing a 9:1 air to acetylene mixture through the pots at 0.5 L min$^{-1}$. After 8 min., 1-mL aliquots of the effluent gas stream were collected from each pot and analyzed for ethylene by gas chromatography. Nitrogenase activity for glyphosate-treated and control plants was similar at 14 DAE, except for Run 4 when ARA was lower for glyphosate-treated plants (Table 5). ARA was 12 to 20% lower for glyphosate-treated plants at 21 DAE in three of the four runs. By 28 DAE, ARA was lower in glyphosate-treated plants only in Run 2 and was greater than control plants in Run 1. These results from the growth cabinet experiment agree with the greenhouse experiment in that nodulation and $N_2$ fixation were generally decreased by early application of glyphosate but subsequently recovered.

TABLE 5

Acetylene reduction activity (mean ± SE) at 14, 21, and 28 DAE† of TV5866RR as
influenced by glyphosate in four growth chamber experiments.

| | Run 1 | | Run 2 | | Run 3 | | Run 4 | |
|---|---|---|---|---|---|---|---|---|
| DAE† | None | Glyph‡ | None | Glyph | None | Glyph | None | Glyph |
| | μmol $C_2H_4$ plant$^{-1}$ h$^{-1}$ | | | | | | | |
| 14 | 32 ± 2 | 33 ± 2 | 27 ± 4 | 23 ± 3 | 59 ± 10 | 57 ± 13 | 38 ± 2 | 28 ± 4* |
| 21 | 40 ± 3 | 45 ± 3 | 66 ± 4 | 53 ± 6* | 90 ± 1 | 75 ± 9* | 64 ± 3 | 56 ± 3* |
| 28 | 61 ± 7 | 76 ± 7* | 91 ± 10 | 70 ± 4* | 131 ± 5 | 115 ± 13 | 116 ± 9 | 107 ± 14 |

†DAE, days after emergence.
‡Plants were treated with 1.68 kg ha$^{-1}$ of glyphosate at 5, 12, and 19 DAE for each run.
*Indicates a significant difference (± two standard errors) between glyphosate-treated and untreated plants, within a run of the experiment and within a measurement date.

Example 2

Comparison of the Sensitivity of Glyphosate Resistant Soybean Cultivars to Glyphosate Differences in sensitivity to postemergence applications of glyphosate were evaluated among five GR soybean cultivars from maturity groups IV and V. Cultivars evaluated were Asgrow A4501RR (A4501RR), Asgrow A5901RR (A5901RR), Delta King 5961RR (DK5961RR), Hartz H5164RR (H5164RR), and TV5866RR. Growing conditions, plant developmental stages at glyphosate application timings, and type of data recorded were the same as in Example 1. Glyphosate was applied to half of the plants at 1.68 kg ha$^{-1}$ on 5, 10, 18, 25, and 32 DAE for a total of 8.4 kg ha$^{-1}$ and plants were harvested at 40 DAE. The other plants were not treated and served as controls. Although the maximum recommended rate for glyphosate within a single soybean crop is 3.36 kg ha$^{-1}$, this high application-rate total was applied in order to accentuate any potential differences in cultivar sensitivity to glyphosate. The experiment was a completely random design with six replications.

Soybean cultivars responded differently to glyphosate applications (Table 6). Root biomass and nitrogen content at 40 DAE were decreased by 25 to 47% for cultivars TV5866RR, A4501RR, and DK5961RR for glyphosate treated plants compared to plants of the control treatment. Nodule mass in DK5961RR and shoot mass in TV5901RR were also decreased by glyphosate treatment. None of the measured biomass or nitrogen parameters were decreased by glyphosate for the cultivars A5901RR or H5164RR, and in fact, nodule biomass for A5901RR was increased for plants in the glyphosate treatment relative to plants from the control treatment.

TABLE 6

Biomass and nitrogen content of GR soybean cultivars at 40 DAE in response to glyphosate in Greenhouse Example 2.

| Cultivar | Glyphosate treatment | Nodule | Biomass Root | Shoot | Nitrogen Root | Shoot |
|---|---|---|---|---|---|---|
| | | g plant$^{-1}$ | | | mg plant$^{-1}$ | |
| TV5866RR | none | 0.43 | 1.20* | 4.25* | 49* | 160 |
| | E + L† | 0.34 | 0.71 | 3.07 | 35 | 131 |
| A4501RR | none | 0.51 | 1.84** | 5.41 | 60* | 201 |
| | E + L | 0.47 | 1.22 | 4.55 | 45 | 185 |
| A5901RR | none | 0.47* | 1.14 | 3.65 | 39 | 163 |
| | E + L | 0.54 | 0.93 | 4.03 | 45 | 163 |
| DK5961RR | none | 0.50** | 1.39** | 4.31 | 52** | 163 |
| | E + L | 0.40 | 0.74 | 3.41 | 31 | 142 |
| H5164RR | none | 0.48 | 1.35 | 4.52 | 48 | 158 |
| | E + L | 0.47 | 1.18 | 4.36 | 46 | 170 |

†Glyphosate at 1.68 kg ai ha$^{-1}$ was applied 5, 10, 18, 25, and 32 DAE in the early plus late (E + L) treatment.
*, ** Indicates a significant difference with a two-sided t-test at the 0.1 and 0.05 level, respectively, between control and glyphosate-treated plants within a cultivar and measurement parameter.

Although glyphosate application timings were different between Examples 1 and 2, the response of GR soybean was similar. In Example 1, plants were treated with glyphosate early and showed decreased biomass and nitrogen content at 19 DAE but had recovered by 40 DAE. In Example 2, continued use of glyphosate (early plus late treatment) between 19 and 40 DAE prevented the recovery seen at 40 DAE in Example 1.

Example 3

Effect of Available Soil Nitrogen on the Response of Glyphosate Resistant Soybean Cultivars to Glyphosate Response of the soybean cultivar DK5961RR to glyphosate with and without available soil nitrogen was evaluated. Treatments were a factorial arrangement of two harvest dates, plus and minus soil nitrogen, and plus and minus glyphosate application. Experimental conditions were similar to those described for Examples 1 and 2, including timing of nutrient applications. At 5 and 12 DAE when soybean were at the V1 and V2 developmental stages (Fehr and Caviness, 1977), respectively, glyphosate was applied at 1.68 kg ha$^{-1}$ to treatments with glyphosate. Plants were harvested at 19 and 40 DAE as described previously. For the plus nitrogen treatment, plants harvested at 19 and 40 DAE received in the nutrient solution at total of 150 and 300 mg N as NO$_3^{-1}$, respectively. The experiment was a randomized complete block with six replications and was repeated.

Dinitrogen fixation did not appear to be the only physiological process inhibited by glyphosate in soybean. Early applications of glyphosate decreased biomass and nitrogen content by 20 to 47% for the cultivar DK5961RR by 19 DAE when grown in the presence of soil nitrogen (Table 7). In treatments without soil nitrogen, glyphosate did not decrease plant biomass or nitrogen content at 19 DAE.

TABLE 7

Effect of glyphosate and soil nitrogen on DK5961RR at Harvest 1 (19 DAE) and Harvest 2 (40 DAE) in Greenhouse Example 3.

| Harvest | Soil nitrogen | Glyphosate† | Biomass Root | Shoot | Nitrogen Root | Shoot |
|---|---|---|---|---|---|---|
| | | | g plant$^{-1}$ | | mg plant$^{-1}$ | |
| 1 | yes | no | 0.38a‡ | 0.76a | 9.66a | 38.8a |
| | | yes | 0.20c | 0.58c | 5.77c | 31.0b |
| 1 | no | no | 0.30b | 0.72ab | 7.31bc | 20.9c |
| | | yes | 0.30b | 0.63bc | 7.53b | 22.2c |
| 2 | avg§ | no | 0.60* | 2.17* | 13.3 | 81.6* |
| | avg | yes | 0.48 | 1.81 | 11.1 | 70.7 |
| 2 | yes | avg | 0.49 | 2.50* | 10.8* | 104.6* |
| | no | avg | 0.58 | 1.48 | 13.6 | 47.8 |

*Indicates a significant difference within a column between nitrogen means or glyphosate means as determined by an F-test (P = 0.05).
†Glyphosate was applied at 1.68 kg ha$^{-1}$ 5 and 12 DAE to plus glyphosate treatments.
‡Means followed by the same letter within a column for Harvest 1 are not significantly different as determined by an LSD (P = 0.05).
§Values were averaged over the treatment effects when an analysis of variance indicated interaction term was NS.

At Harvest 2 (40 DAE), the soil nitrogen by glyphosate treatment interaction was not significant (P=0.66) for plant biomass or nitrogen content, indicating that plants responded similarly to glyphosate with or without soil nitrogen. Glyphosate decreased root and shoot biomass 17 to 20% and shoot nitrogen content 13%, averaged across soil nitrogen treatments (Table 7). Plants grown on nutrients containing nitrogen were larger than those dependent upon N$_2$ fixation, and the root to shoot ratio was very different. Soil nitrogen increased shoot weight by 70% over plants that received no soil nitrogen, but root weight was not significantly different between nitrogen treatments. Similarly, total shoot nitrogen for plants from the plus soil-nitrogen treatment was more than double that from the minus nitrogen treatment, whereas root nitrogen content was greater for plants grown without soil nitrogen. While not wanting to be bound by any particular mode of action, these results indicate that glyphosate affects plant growth regardless of plant nitrogen source, that plants supplemented with nitrogen fertilizer are larger than those dependent on N$_2$ fixation, and that the detrimental effects of glyphosate on plants dependent upon N$_2$ fixation can be partially compensated by soil nitrogen availability.

Example 4

Effect of Glyphosate on Response of Nitrogenase Activity to Soil-Water Deficits The effects of glyphosate on the response of nitrogenase activity to soil-water deficits in the cultivar TV5866RR were evaluated in a growth cabinet. Plants were established in flow-through pots (Purcell et al., 1997) for nondestructive measurement of acetylene-reduction activity (ARA) as an indicator of relative nitrogenase activity. Pots were constructed of 10-cm-diameter, 40-cm-long polyvinyl chloride pipe, sealed at the bottom and top with end caps. Fittings were inserted into the bottom for drainage and introduction of air samples during ARA measurements, and into the top for air exhaust and sampling. Pot tare weights were recorded prior to adding potting mixture. Potting media and nutrients were the same as described in Examples 1–3. Pots were filled with potting media, saturated with DI water, and 1 L of N-free nutrients was added to each pot. After allowing excess water to drain for 12 h, pot capacity weights were recorded.

A single plant was grown through a hole in the top of each pot. Inoculum was added to the soil at planting and after emergence as described in Example 1. The growth chamber was maintained at 24 C, and light was supplied by fluorescent and incandescent lamps with an intensity at the top of the plant of approximately 500 $\mu mol^{-2}s^{-1}$ photosynthetically active radiation. Treatments consisted of control and glyphosate-treated plants. Glyphosate was applied at 1.68 kg ha$^{-1}$ on 5, 12, and 19 DAE at the V1, V2, and V4 developmental stages, respectively, to glyphosate-treated plants as described in Example 1.

ARA was measured beginning 28 DAE by introducing a 9:1 air to acetylene mixture at 0.5 L min$^{-1}$ into the bottom of the pots that were sealed around the plant root system. The acetylene mixture was exhausted from the fitting in the top of the pot. After 8 min, when the ethylene concentration in gas exhausted from the pots was constant, samples were collected from the efflux of each pot with 1-mL syringes. Ethylene concentration in the gas samples was quantified by gas chromatography using a flame ionization detector and a Porapak N column (de Silva et al., 1996). After the 8-min acetylene exposure, acetylene was removed from the gas stream and pots were flushed with air for approximately 60 min. This assay system has been shown to result in no acetylene-induced decline of nitrogenase activity (Minchin et al., 1983). Ethylene concentrations were expressed as $\mu mol\ C_2H_4\ plant^{-1}h^{-1}$, and means within an experiment and sample date were compared using standard errors. The experiment was repeated three times using a completely random design with Runs 1 and 24 having four replicates and Runs having six replicates each of glyphosate-treated and untreated-control plants.

At 28 DAE, half of the glyphosate-treated and control plants were designated well watered or water deficit treatments. Well-watered plants received daily the amount of water that they lost through transpiration whereas plants of the water-deficit treatment were allowed to progressively lose water over a 7-day period. Plants were of the water-deficit treatment were weighed each day, and the soil moisture content was adjusted to the same level by adding appropriate amounts of water to each pot.

Soil-water data were converted from pot capacity weight to fraction of the transpirable soil water (FTSW) (de Silva et al., 1996). Transpirable water was calculated as the difference between the soil capacity weight and the soil weight when transpiration for water-deficit plants was less than 10% of the well-watered plants (Ritchie, 1981). Soil weight at zero transpirable water was determined to be 0.24 of the soil weight at pot capacity. Daily target weights were converted to FTSW according to the equation:

$$FTSW=(1.32 * \text{fraction of pot capacity soil weight})-0.32.$$

ARA was measured daily between 1000 and 1200 h for all plants during the drying period. ARA values were double normalized according to Ray and Sinclair (1997) to give "Relative ARA." The first normalization corrected for differences in activity among individual plants prior to initiation of water-deficit treatments, and the second normalization minimized effects of fluctuations in ARA for control plants (well watered, no glyphosate) among days. As a result, Relative ARA was 1 for all plants at the beginning of the experiment and was approximately 1 for the control plants throughout the experiment. Relative ARA values among glyphosate and water treatments within a day were compared using standard errors.

ARA was more sensitive to water deficits for glyphosate-treated than for untreated plants (FIG. 1). Relative ARA for water-deficit plants was not significantly different from well-watered plants until FTSW was below 0.27. At FTSW of 0.21, untreated plants had nitrogenase activity 88% of the well-watered plants while glyphosate-treated plants with the same amount of available water had nitrogenase activity of 71% of the well-watered control. This relationship of greater sensitivity of nitrogenase activity to water deficits of glyphosate-treated compared to untreated plants was also evident at FTSW values of 0.14 and 0.11. Relative transpiration was not different between glyphosate-treated and untreated plants, indicating that differences in water extraction did not account for the increased sensitivity to water deficit in glyphosate-treated plants.

Example 5

Effect of Foliar Applications of Glyphosate to Glyphosate Resistant Soybean Cultivars under Field Conditions.

Field experiments were conducted at Fayetteville and Keiser, Ark., to evaluate the response of GR soybean cultivars to foliar applications of glyphosate under field conditions susceptible to drought stress. Although extensive research on the effects of glyphosate on soybean in relatively high yield environments (2000 to 4000 kg ha$^{-1}$) have indicated that there is no effect of glyphosate relative to untreated plants under weed free conditions (Delannay et al., 1995), there have been no published reports evaluating the effects of glyphosate specifically under low yield and drought-prone environments. Delannay et al. (1995) reported three experiments out of 58 in which yields were less than 1500 kg ha$^{-1}$, but there was no indication as to the cause of these low yields. The Fayetteville experiment was conducted on a Pembroke silt loam (Ultic Paleudalfs) on 15-cm-high beds spaced 1 m apart. Water was applied as needed until mid-reproductive development (R5) with sprinkle irrigation. At Keiser the soil was a Sharkey silty-clay (Vertic Haplaquepts), and soybean was planted on a flat seedbed with rows 0.96 m apart. Irrigation was applied with an overhead, lateral-move system.

Experiments at both locations were a factorial of two cultivars and five herbicide treatments in a randomized complete block design with four replications. Plots were four rows wide by 9 m long. A5901RR and DK5961RR were chosen to represent the least and most sensitive to glyphosate of the GR soybean cultivars evaluated in Example 2. The seeding rate was 370,000 ha$^{-1}$ at both locations.

Herbicide treatments were: i) weed-free check, ii) glyphosate at 7 and 21 DAE, iii) glyphosate at 7 DAE and at R2, iv) glyphosate at 21 and 35 DAE, and v) acifluorfen {5-[2-chloro-4-(trifluoromethyl)phenoxy]-2-nitrobenzoic acid}plus bentazon [3-(1-methylethyl)-(1H)-2, (3H)-one 2,2-dioxide] at 7 DAE (included as a standard herbicide comparison). Herbicides were applied as a broadcast treatment, sprayed over-the-top of the canopy with a $CO_2$-powered backpack sprayer in a volume of 93 L ha$^{-1}$. Glyphosate was applied at 1.68 kg ha$^{-1}$ at each timing, and acifluorfen and bentazon were applied at 0.42 and 0.84 kg ai ha$^{-1}$, respectively. All herbicide treatments contained appropriate surfactants. Plants were at V1, V4, and V9 development stages at 7, 21, and 35 DAE application timings, respectively, at both locations. R2 applications were made at 45 and 48 DAE at Fayetteville and Keiser, respectively. Plots were maintained weed free by hand weeding as needed. Four replications of the non-nodulating isoline of the cultivar 'Lee' were included at each location as an indicator of plant-available soil nitrogen.

Above-ground biomass was collected from 1 m$^2$ from the center two rows of each plot 14, 35, 49, and 70 DAE at both locations and 91 DAE at Keiser. Samples were prepared and analyzed for total nitrogen as previously described. Seed yield was determined by harvesting 4.5 m from each of the center two rows. Average seed mass was determined from a random sample of 100 seeds. Biomass data were evaluated by comparing the means±standard errors between herbicide treatments within a cultivar and sample date. Seed yield and 100 seed weight data were analyzed by location and cultivar using analysis of variance, and significant differences were based on an LSD (P<0.05).

Growth of the Lee non-nodulating cultivar indicated differences in plant available soil nitrogen between the Fayetteville and Keiser locations. At the final biomass harvest, Lee non-nodulating had accumulated 40 to 50% as much nitrogen and 63 to 70% as much biomass as the weed-free check for the other two cultivars at Keiser. At Fayetteville, nitrogen and biomass accumulation by Lee non-nodulating were approximately 65 and 76%, respectively, of the weed-free checks for the $N_2$-fixing cultivars. These data indicate that available soil nitrogen was greater at the Fayetteville location, decreasing the dependence of soybean on $N_2$ fixation as a nitrogen source compared with the Keiser location.

Figure 2A:
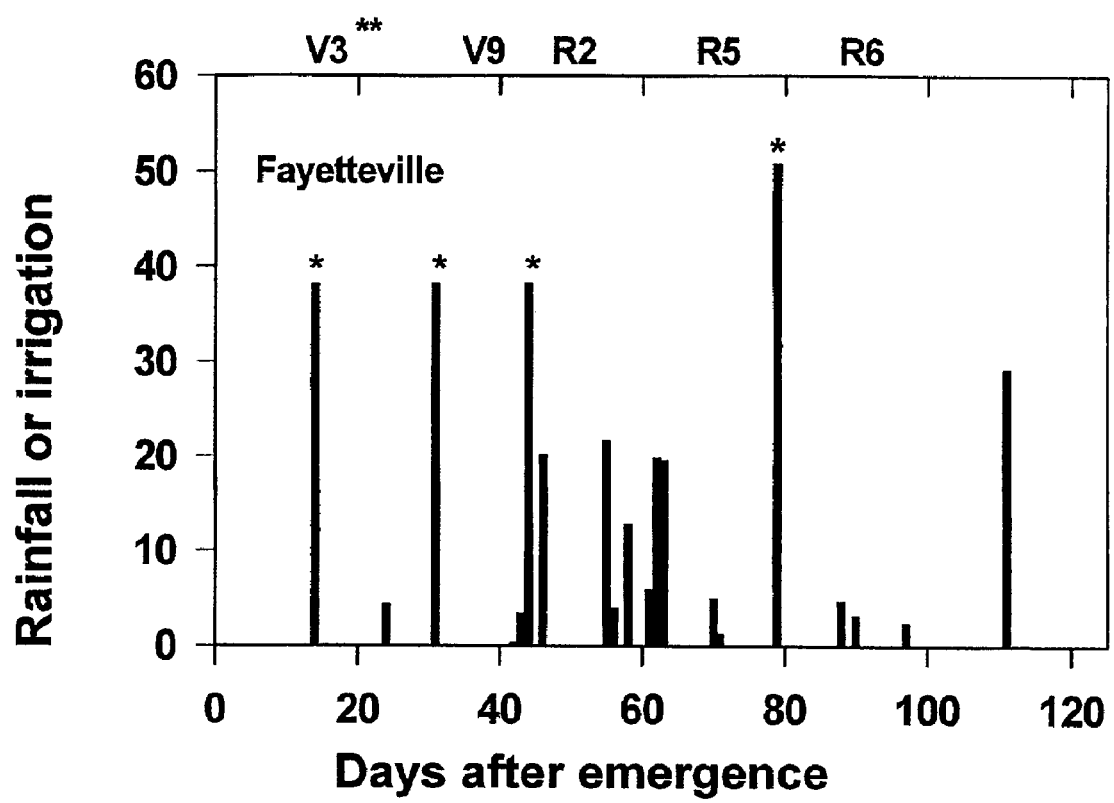
FIGS. 2A and B show rainfall, irrigation (*), and soybean growth stages (**) for Fayetteville and Keiser field experiments. At Fayetteville, the growing season ended at 104 days after emergence (DAE) due to freezing temperatures.
Figure 2B:
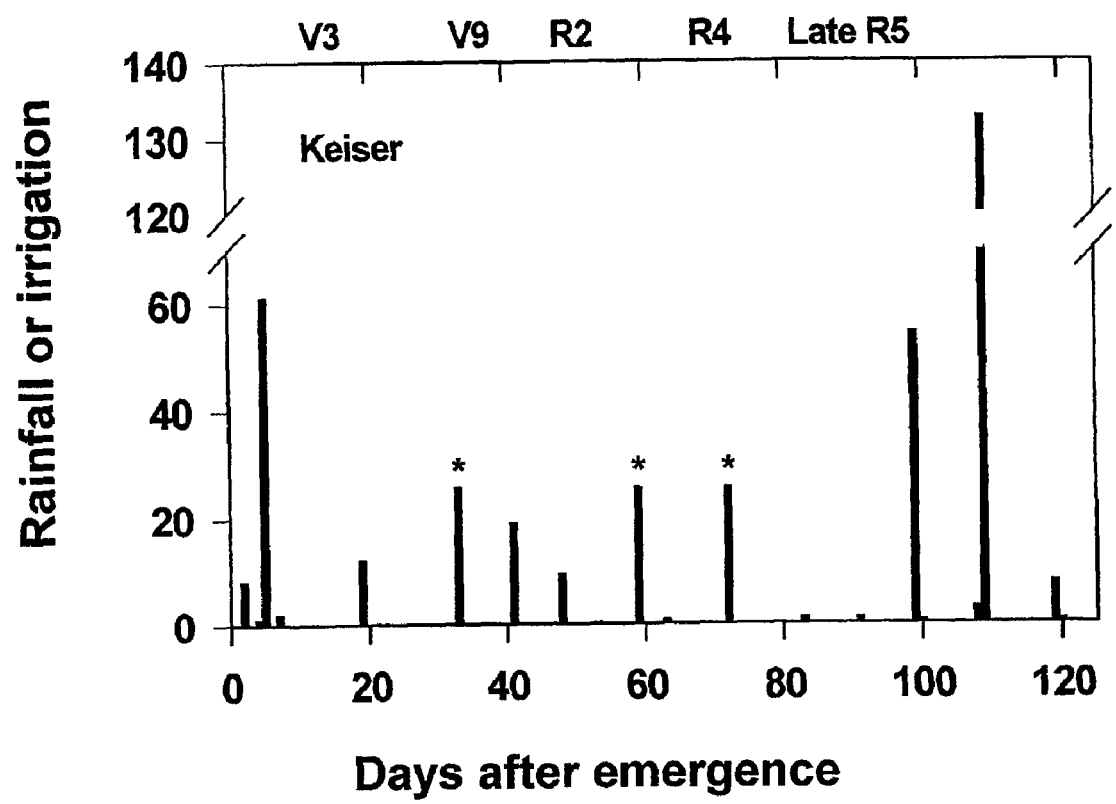
Figure 3A:
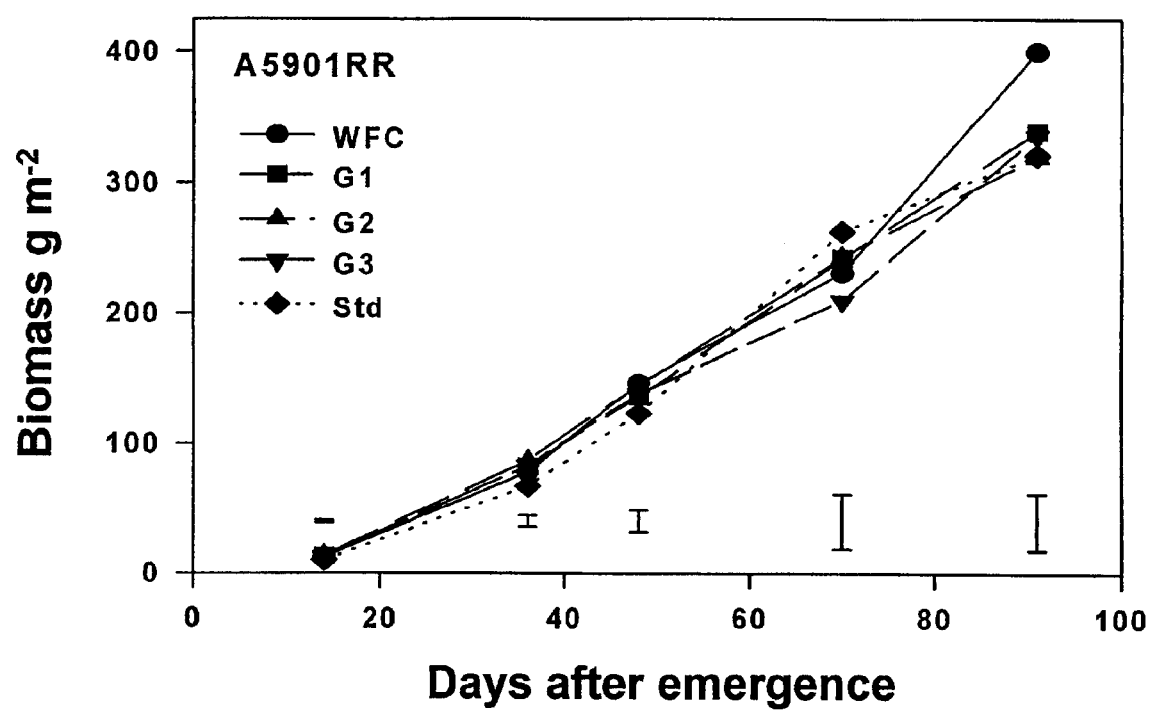
FIGS. 3A and B show biomass of GR soybean cultivars in response to herbicide treatments in the Keiser field experiment. Treatments were: WFC, weed-free check; G1, glyphosate applied 7 and 21 days after emergence (DAE); G2, glyphosate at 7 DAE and R2; G3, glyphosate at 21 and 35 DAE; and Std, acifluorfen plus bentazon standard at 0.42 plus 0.84 kg ha$^{-1}$ at 7 DAE. Each glyphosate application consisted of glyphosate at 1.68 kg ha$^{-1}$. Error bars represent two standard errors for comparison among herbicide treatments within a sample date.
Figure 3B:
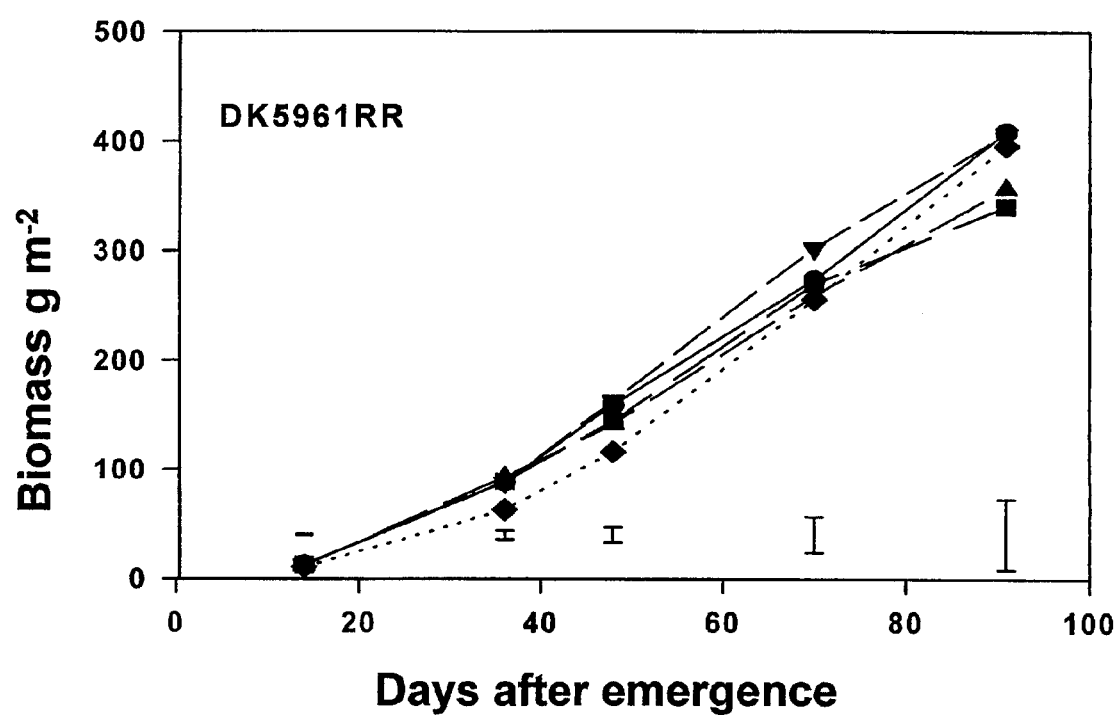

None of the herbicide treatments affected biomass or nitrogen accumulation, 100 seed weights, or yield (Table 8) at Fayetteville, where there was adequate soil water from rainfall or irrigation throughout the season (FIG. 2). At Keiser, herbicide treatments did affect nitrogen and biomass accumulation. There was no effect of herbicide treatment on shoot nitrogen concentration within a sample date; therefore, only biomass data are presented. The standard herbicide treatment of acifluorfen plus bentazon slightly decreased biomass of both cultivars during vegetative growth at 35 and 48 DAE (FIG. 3). By early reproductive growth, at 70 DAE, biomass for all herbicide-treated plots was equal to the untreated check.

TABLE 8

Soybean seed yield as influenced by herbicide treatment and cultivar in field experiments at Keiser and Fayetteville, Arkansas, in 1999.

| Herbicide treatment | Application dates | Keiser | | Fayetteville | |
| --- | --- | --- | --- | --- | --- |
| | | A5901RR | DK5961RR | A5901RR | DK5961RR |
| | DAE | | | kg ha$^{-1}$ | |
| none | — | 1291a† | 1296a | 2084a | 1874a |
| glyphosate 1‡ | 7 & 21 | 974b | 1197ab | 2053a | 1854a |
| glyphosate 2 | 7 & 49 | 1138ab | 989b | 2057a | 1798a |
| glyphosate 3 | 21 & 35 | 1050ab | 1291a | 1999a | 1992a |
| standard§ | 7 | 1075ab | 1362a | 1936a | 1917a |

†Means within a column followed by the same letter are not significantly different as determined by an LSD (P = 0.05).
‡Glyphosate treatments consisted of an application of 1.68 kg ha$^{-1}$ at each of the indicated timings.
§The standard herbicide treatment consisted of acifluorfen plus bentazon applied at 0.42 plus 0.84 kg ha$^{-1}$.

There was adequate soil water at the Keiser location until the 70 DAE biomass harvest (FIG. 2). Following a 25-mm irrigation applied 72 DAE, there was no significant rainfall or irrigation for 27 days, until 99 DAE. During this time, the untreated checks generally continued to increase biomass at a greater rate than herbicide-treated plants (FIG. 3). Decreased root growth and soil-water extraction may have contributed to the increased sensitivity of glyphosate-treated plants to water deficits that occurred at the Keiser location. For A5901RR, all glyphosate-treated and standard herbicide-treated plots had significantly less biomass at 92 DAE than the untreated check. Although there were no significant differences in biomass for DK5961RR at 92 DAE, biomass for plots treated with glyphosate at 7 followed by 21 DAE or at 7 followed by 49 DAE tended to be lower than other treatments.

At Keiser, seed yields tended to reflect the differences in biomass seen at 92 DAE (Table 8). A5901RR yields from herbicide-treated plots were 12 to 25% lower than from the untreated check, but only the glyphosate at 7 followed by 21 DAE treatment had a significantly lower yield than the check. DK5961RR yield was significantly decreased (24%) by glyphosate applied at 7 followed by 21 DAE, and yield from plots sprayed with glyphosate at 7 followed by 49 DAE was numerically lower (8%) than the untreated check. These two treatments also had a tendency for decreased biomass, though not significantly, at the 92 DAE biomass harvest (FIG. 3). Seed yields of DK5961RR from other glyphosate and standard herbicide treatments were numerically equal to the untreated check (Table 8).

Although these cultivars responded differently to multiple glyphosate applications when grown under well-watered conditions in the greenhouse, they responded similarly under field conditions. This indicates that genotypic differences in sensitivity to glyphosate may depend upon the number of applications, application rate and timing, and the subsequent plant-growth environment.

Example 6

Identification and Selection of Glyphosate Resistant Strains of $N_2$ fixing Bacteria Selection of *B. japonicum* that is resistant to glyphosate may be accomplished by means known in the art, such as by challenging *B. japonicum* with glyphosate concentrations that are inhibitory to the wild type. *B. japonicum* (strain USDA 110) was grown in defined liquid media lacking amino acids (Karr and Emerich, 1989) on a rotary shaker at 25 C with concentrations of glyphosate up to 10 mM. The defined media consists of 25 mM arabinose as the carbon source, 15 mM $(NH_4)_2SO_4$, 0.7 mM $MgSO_4$, 0.4 mM $CaCl_2$, 20 mM NaCl, 2.5 mM $K_2HPO_4$, and 40 mM MOPS (3-[N-morpholino]propane-sulfonic acid), at pH 6.8, plus the appropriate micronutrients. At a glyphosate concentration of 10 mM, *B. japonicum* growth after 9 days was inhibited approximately 90% compared to the control without glyphosate. From the 10 mM glyphosate culture, *B. japonicum* was streaked onto agar plates (1.5% agar) containing the defined media and 10 mM glyphosate. Forty-five individual colonies were identified from these plates that grew in the presence of 10 mM glyphosate. These colonies were removed and stored in frozen culture in 50% sterile glycerol.

The glyphosate resistance of selected colonies is determined by comparing their growth with the wild-type bacteria over a range of glyphosate concentrations, as shown in Example 12. Increased kinetic constant of inhibition to glyphosate for EPSPS in selected *B. japonicum* strains compared with the wild type strain is also an indication of resistance.

Example 7

Glyphosate Resistance is Unlikely to Occur Among Indigenous Soil Populations of Rhizobia Frozen cultures from Example 6 were thawed and grown in 5 mL of liquid Tulley's culture (minus glyphosate). Liquid cultures were adjusted to an $OD_{600}$ of 0.16, and 100 uL was added to 5 mL of Tulley's media containing 5 mM glyphosate. Duplicate cultures were evaluated from each of the original colony selections. Wild type USDA 110 in the presence and absence of glyphosate was used as a control. The cultures were allowed to grow for 14 days, and then the OD of each culture was measured.

After 14 days, glyphosate inhibited all bacterial growth of colonies selected in Example 6 (Table 9). The cultures that were selected from the agar media containing glyphosate did not show growth that was significantly different from the wild type USDA 110 grown in the presence of glyphosate. The selected cultures also did not show differences between individual colonies. Averaged over all, of the 45 colonies originally selected for growth on agar plates containing glyphosate, growth in liquid culture in the presence of glyphosate was 27% of the growth of wild type USDA 110 in the absence of glyphosate. In comparison, growth of USDA 110 in the presence of glyphosate was 33% of USDA 110 in the absence of glyphosate.

TABLE 9

Growth of selected *B. japonicum* cultures after 14 days in the absence (−) or presence (+) of 5 mM glyphosate.

| Strain | Glyphosate | $OD_{600}$ |
| --- | --- | --- |
| USDA 110 | − | 1.33 a[†] |
| USDA 110 | + | 0.44 b |
| Selected[‡] | + | 0.36 b |

[†]Means followed by the same letter within a column are not significantly different (P = 0.05)
[‡]Forty individual cultures of USDA 110 were selected based upon their ability to form colonies on agar media containing glyphosate. There were no significant differences among selected strains, and an $OD_{600}$ is presented that was averaged over all strains.

The fact that colonies that were selected to grow on agar containing 10 mM glyphosate were not able to retain the ability to grow in the presence of glyphosate in liquid culture indicates that they were not resistant to glyphosate. The enzyme affected by glyphosate, 5-enolpyruvylshikimate-3-phosphate synthase (EPSPS), is not mutagenized easily to a resistant form (Bradshaw et., 1997), and single-base pair changes are not effective in creating a resistant EPSPS. The inability to select for glyphosate resistant *B. japonicum* in culture also indicates that glyphosate resistance is not conferred by single base pair changes in the EPSPS gene.

The inability to select for glyphosate resistant *B. japonicum* using the methods described above, or through minor or single base-pair changes, indicates that glyphosate resistance is also unlikely to occur among indigenous soil populations of *B. japonicum* that are challenged with glyphosate in the roots of glyphosate-treated, glyphosate resistant or tolerant soybean. In this case, indigenous *B. japonicum* would not develop glyphosate resistance, and *B. japonicum* genetically engineered for glyphosate resistance would retain the competitive advantage over indigenous strains for nodulation in glyphosate resistant or tolerant soybean that was treated with glyphosate.

The glyphosate resistant EPSPS gene used in glyphosate resistant soybean was derived from Agrobacterium spp. Strain CP4 (Horsch et al., 1988), and this gene is substantially different from that found in most organisms. Therefore, *B. japonicum* resistance to glyphosate will likely require genetically engineering the bacteria with a glyphosate resistant EPSPS gene, similar to that found in *Agrobacterium* spp. Strain CP4 (Horsch et al., 1988). Alternatively, glyphosate resistance in *B. japonicum* may be conferred by increasing the rate at which glyphosate is catabolized. The catabolism of glyphosate to aminomethyl-phosphonic acid (AMPA) has been documented in both Pseudomonas (Jacob et al., 1988) and *Arthrobacter atrocyaneus* (Pipke et al., 1988). The gene coding for the enzyme that breaks down glyphosate, glyphosate oxidoreductase, has been cloned and introduced into several plant species, where it confers high levels of glyphosate resistance (U.S. Pat. No. 5,776,760). Glyphosate resistance in *B. japonicum* is conferred by genetically engineering and expressing high levels of either glyphosate resistant EPSPS or engineering and expressing glyphosate oxidoreductase in *B. japonicum*.

Example 8

Construction of Glyphosate Resistant Strains of $N_2$ Fixing Bacteria.

The present invention is demonstrated with the use of glyphosate resistant *B. japonicum* which is genetically engineered by incorporation of a gene for glyphosate resistant EPSPS. Although use of the gene that was originally isolated from *Agrobacterium* spp. CP4 (Horsch et al., 1988; U.S. Pat. Nos. 4,940,835 and 4,971,908) is a preferred embodiment, a substantially homologous gene may be used (U.S. Pat. No. 5,094,945). For example, polynucleotides that hybridize to mutant EPSPS polynucleotide sequence, particularly under stringent conditions, may be employed. Other nucleotide sequences known in the art may also be used, such as the gene responsible for glyphosate breakdown, glyphosate oxidoreductase (U.S. Pat. No. 5,776,760) or the DNA molecule encoding a mutant aroA gene (ATCC accession number 39256) as disclosed in U.S. Pat. Nos. 4,769,061; 4,971,908; and 5,094,945. Likewise, other rhizobial species may be employed, such as *B. japonicum* subspecies 1 and 2, *B. elkanii*, and *S. fredii*. The *B. japonicum* strain to be transformed could be any strain, including one which demonstrates enhanced nodulation or other desirable trait, either recombinantly or in its native state.

The step of transferring the gene of interest to *B. japonicum* may be carried out by conventional genetic transfer techniques known in the art, including electroporation (Guerinot et al., 1990), conjugation (Loh et al., 1999), biparental mating (Acuna et al., 1987; Loh et al., 1999), or by triparental mating according to the method of Lang et al. (1982).

The preferred integration vector is that described by Acuna et al. (1987), pRJ1035; however, other vectors may be utilized in the practice of the present invention, depending on the specific application. The pRJ1035 plasmid has an EcoR1 and Sma1 cloning site and a kanamycin resistance gene (npt11 gene). Additionally, the vector can be readily multiplied and manipulated in standard *E. coli* strains. On either side of the cloning site are regions homologous to two inverted repeats that are found upstream of the nifDKEN operon in *B. japonicum*. The homologous regions allow for site directed incorporation (by double recombination) of the glyphosate resistant EPSPS gene or glyphosate oxidoreductase gene into the *B. japonicum* chromosome without interrupting an existing gene. Importantly, once the plasmid is inside *B. japonicum*, the plasmid is unable to multiply, and expression of gene of interest is due to stable integration of the gene of interest into the bacterial chromosome.

Construction of the vector containing the glyphosate resistance gene, such as the EPSPS gene or glyphosate oxidoreductase gene, is through standard cloning procedures. For both of the identified genes, only the DNA sequence coding for the structural gene is cloned into the vector; leader sequences and eukaryotic promoters are not required. Upstream regulatory elements, promoter sequences, and transcription termination sequences are cloned into pRJ1035 from pMDH9.0, which contains a cluster of genes from *B. japonicum* coding for several enzymes of the tricarboxylic acid pathway (Green and Emerich, 1997).

The engineered plasmid with DNA of interest enters *B. japonicum* cells by, for example, electroporation or bacterial mating. In the electroporation technique (Guerinot et al., 1990), the permeability of the cell wall to plasmid DNA is increased by repeatedly washing *B. japonicum* cells in sterile cold (4° C.) water in decreasing volumes of water to a density of $10^9$ to $10^{10}$ cells per mL. For each mL of concentrated cells, 12 ng of plasmid DNA is added, vortexed, and placed in a prechilled cuvette with inter-electrode distances of 0.2 cm. An electric field of 12.5 kV/cm is applied for 5 msec, and cells are immediately diluted with 1 mL of nonselective medium and incubated at 30° C. for 20 h. Following incubation, 20 μL of the culture is plated on defined agar (1.5%) medium containing 10 mM glyphosate (as described in Example 6).

For bacterial mating, the cloned gene, such as the glyphosate resistant EPSPS or glyphosate oxidoreductase gene, with appropriate promoter and termination sequences, is first used to transform *E. coli*, strain S17.1. Transformed cells are selected on LB media containing 100 μg/mL kanamycin (Hahn and Hennecke, 1984). Two and one-half mL of *E. coli* culture containing approximately $10^9$ transformed cells is then mixed with one-half mL *B. japonicum* culture containing approximately an equal number of cells. The mixed cells are placed onto a nitrocellulose filter and incubated for two days on agar media containing 200 μg/mL of spectromycin (to select against the donor *E. coli*) and 500 μg/mL of kanamycin or 10 mM glyphosate (to select for the transformed *B. japonicum*). After 7 to 10 days of incubation, individual colonies are selected for purification and characterization.

Further characterization of *B. japonicum* cultures selected as transformants (by either electroporation or biparental mating) is accomplished by dot-blot hybridization (Green and Emerich, 1997). Individual colonies are grown in defined liquid culture, and once they reach the mid-log phase of growth, 1 mL from each colony is applied to each well of a dot-blot apparatus (Bio-Rad) and transferred to a hybridization membrane. Cells on the membrane are lysed, and the membrane is baked to immobilize the DNA. The membranes are then hybridized with radio labeled DNA from the genes of interest, and washed and exposed to x-ray film. Colonies containing either of the inserted genes are visualized as exposed regions on the film. More thorough characterization of the DNA from engineered colonies is made by Southern hybridization (Southern, 1975) by probing with the gene of interest and with a portion of pRJ1035 generally not incorporated into the bacterial chromosome by double recombination. A positive signal from the gene of interest and a negative signal from the plasmid is indicative of a double recombination event. A positive signal from both the gene of interest and the plasmid indicates a single recombination event and is likely to be unstable. Expression of the gene of interest is characterized by hybridization of the specific gene with mRNA in a Northern hybridization.

Example 9

Evaluation of Selected or Genetically Engineered Resistant Strains for Ability to Fix $N_2$ in Symbiotic Relationship with Soybean Cultivars.

Documenting the symbiotic effectiveness of *B. japonicum* strains, which have been selected, mutagenized or engineered for glyphosate resistance is particularly important because the possibility exists that the presence of the glyphosate resistant EPSPS gene in the bacterial chromosome could interfere with processes leading to an effective symbiosis. The symbiotic effectiveness for enhanced N2 fixation of *B. japonicum* strains selected (Example 6) or engineered (Example 8) for glyphosate resistance are evaluated by growing glyphosate resistant or tolerant soybean in sterile soil that is then inoculated with desired strains of *B. japonicum*. Glyphosate resistant or tolerant soybean seeds are treated with glyphosate (Example 13) or the plants are sprayed foliarly with glyphosate as described in Example 1, or other methods known in the art may be employed (Daramola et al., 1994). The effects on plant growth, nodulation, and $N_2$ fixation are compared to the wild-type strain.

Alternatively, symbiotic effectiveness for enhanced N2 fixation of selected or engineered *B. japonicum* strains are evaluated by nondestructive measurements of acetylene reduction activity (ARA). The procedure is as described in Example 1 with the additional step that potting media and pots are sterilized prior to inoculating with desired *B. japonicum* strains. Repeated measurements of ARA are made during the course of development as a measure of nodule activity and how quickly an effective symbiosis is established.

Example 10

Competitive Advantage Conferred by Glyphosate Resistant Strains of *B. japonicum* Compared to Indigenous Bacterial Populations on Glyphosate Resistant Soybean treated with Glyphosate The competitive advantage of glyphosate resistant *B. japonicum* strains with indigenous strains which are not resistant is compared by nodule occupancy studies similar to those described by Kuykendall et al. (1996) or as described in U.S. Pat. No. 4,863,866 (Both references incorporated herein by reference). In greenhouse experiments, soybean plants are grown in sterile soil, treated with glyphosate foliarly (Example 1) or by seed treatment (Example 13), and inoculated with known ratios of a glyphosate resistant strain to other specific strains.

It is broadly intended within the scope of the present invention that the bacterial inoculant of the present invention be inoculated into the soil with soybean seeds so that a bacterial culture will develop an intimate attachment to the root system of the plant as it grows. To facilitate this co-culturing, it is preferable that viable cells of the inoculant, preferably diluted with a suitable extender or carrier, either be applied to the seeds prior to planting or be introduced into the seed furrows at the time of planting the soybean seeds. The bacterial strains, with or without a carrier, can be provided as an inoculant to be used as a seed treatment or may be inserted directly into the furrows into which the soybean is planted as it is planted.

Whether the bacterial strains are coated actually on the soybean seeds or are inserted into the furrows, the inoculant is preferably diluted with a suitable carrier or extender so as to make the bacterial strain easier to handle and to provide a sufficient quantity of material so as to be capable of easy human handling. Examples of suitable carriers include clay, vermiculite, perlite, charcoal, and water (aqueous solution). As those of skill in the art will recognize, inoculation may be accomplished by other methods known in the art (U.S. Pat. No. 5,922,316 incorporated herein).

The density of bacterial inoculation onto the seed or into the furrow should be sufficient to populate the sub-soil region adjacent to the roots of the soybean plants. An effective amount of bacterial inoculant should be used. That amount is the amount sufficient to populate the root environment sufficiently to increase overall $N_2$ fixation.

Initially, a glyphosate resistant strain such as that derived from strain USDA 110 is compared with the wild-type strain at dilutions (based on optical densities at 660 nm) of 1:10, 1:1, and 10:1. Other dilutions are used, as necessary. After 3 to 4 weeks of plant growth, plants are harvested destructively to measure any strain effect on plant mass and plant nitrogen. A representative proportion of nodules from each plant is harvested, surface sterilized, and the specific strain occupying each individual nodule determined (Kuykendall et al., 1996; Fuhrmann and Vasilas, 1993, incorporated herein by reference) using appropriate antibiotic markers, serological characteristics, and/or DNA characterization techniques. Alternative studies, such as adaptations of those described in U.S. Pat. No. 5,173,424, are used to evaluate the effect of a glyphosate resistance gene on the competitiveness of glyphosate resistant *B. japonicum* strains. Similar experiments are performed in the greenhouse on dominant strains found in the indigenous population. Field experiments are also conducted to characterize plant growth and nodule occupancy following inoculation with glyphosate resistant *B. japonicum* strains on soybean treated with glyphosate.

Example 11

Comparison of Plant Growth, Productivity and Grain Yield in Soybean Cultivars Grown with and without Glyphosate Resistant $N_2$ Fixing Bacteria Field experiments, similar to those described in Example 10, are conducted to evaluate plant growth, productivity, and grain yield of glyphosate resistant or tolerant soybean treated with glyphosate and inoculated with superior $N_2$ fixing *B. japonicum* that is resistant to glyphosate. Selected or engineered *B. japonicum* strains are used to inoculate soybean as an in-furrow treatment at planting or as a peat-based seed treatment. Soybean is treated with glyphosate foliarly as described in Example 1, or by treating the seeds as described in Example 13. Treatments with glyphosate resistant *B. japonicum* strains are compared to indigenous *B. japonicum* and standard inoculants. $N_2$ fixation in the crop with different inoculant treatments is measured by including a non-nodulating soybean line as a reference crop, and sampling a bordered area repetitively over several weeks. By subtracting the g N m$^{-2}$ d$^{-1}$ in the non-nodulating crop from the g N m$^{-2}$ d$^{-1}$ an estimate is made of the nitrogen derived from $N_2$ fixation (Talbott et al., 1985). The advantage derived from increased competitiveness of glyphosate resistant *B. japonicum* strains is measured by seed yield increases relative to indigenous *B. japonicum*.

Example 12

Comparison of *Bradyrhizobium Japonicum* Growth in Culture without Glyphosate and with Increasing Dosages of Glyphosate

Figure 4:
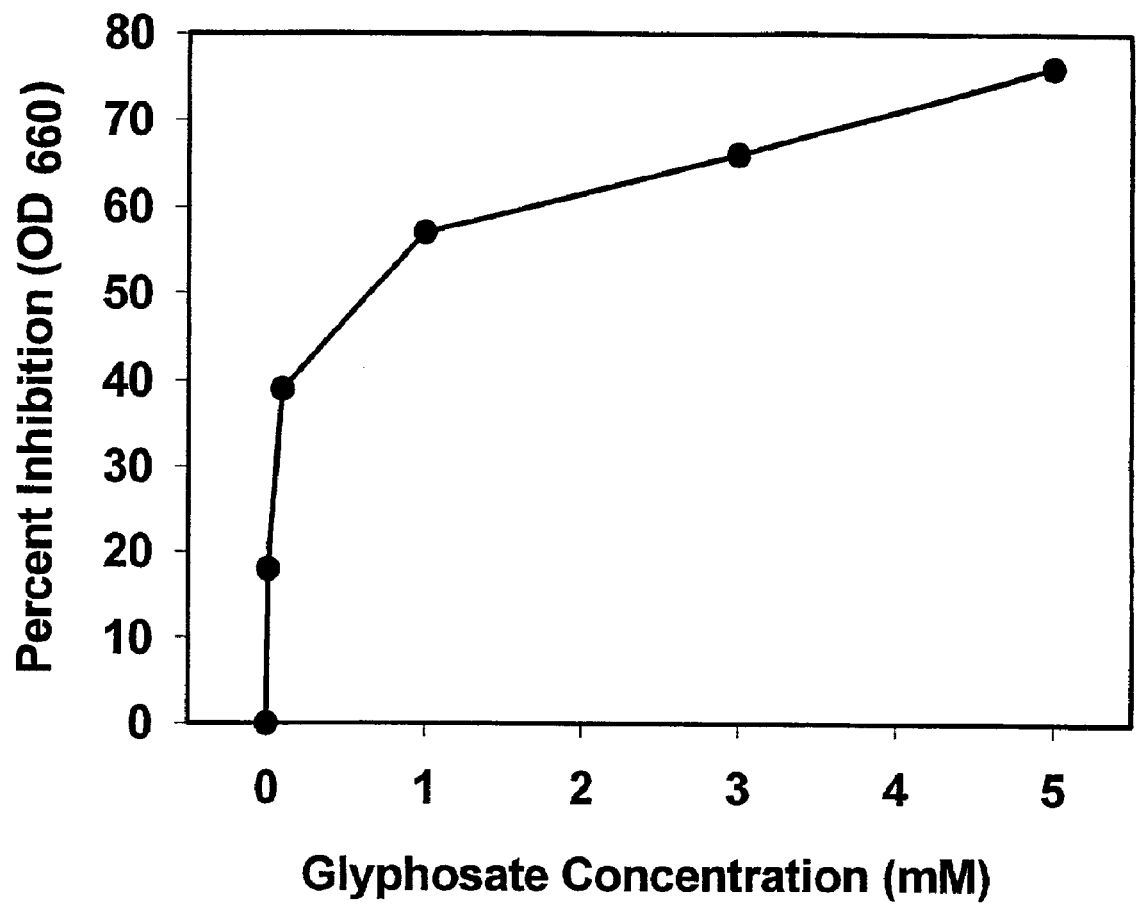
FIG. 4 shows growth inhibition of *B. japonicum* (Strain USDA 110) following 7 days of growth in a defined media lacking amino acids in response over a range of glyphosate concentrations from 0 to 5 mM.
Figure 5A:
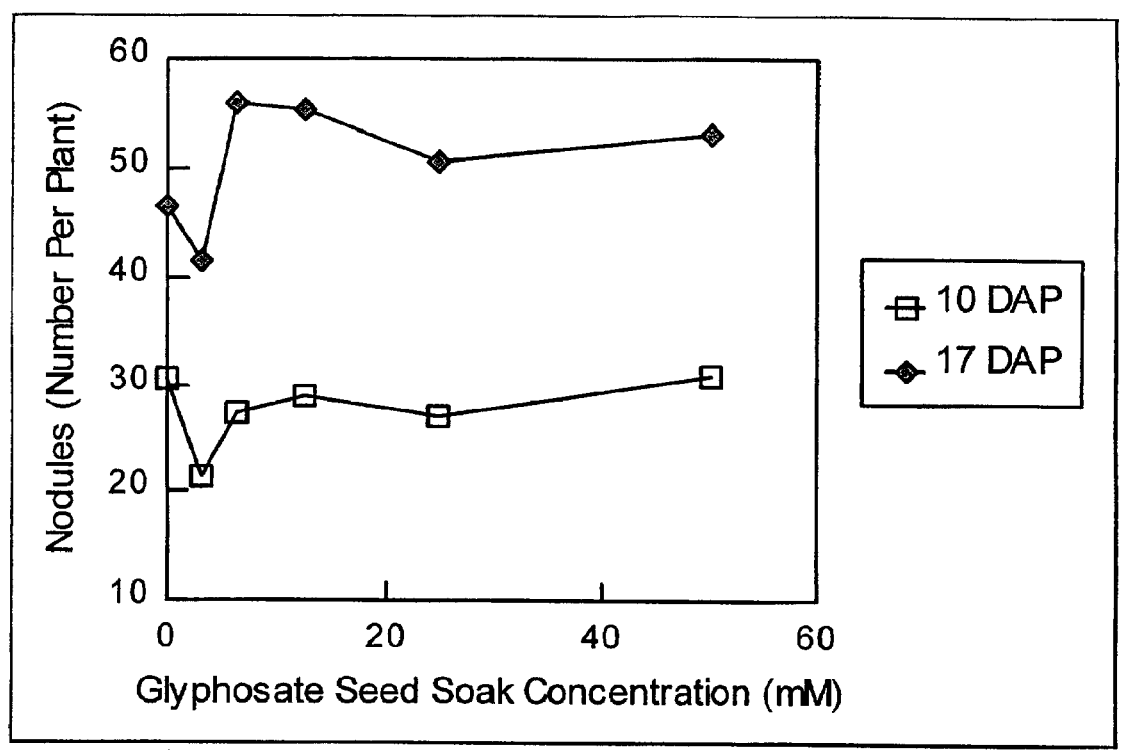
FIGS. 5A–D show the effect of imbibing seed in a range of glyphosate concentrations for two hours and the subsequent effect this has on nodule number (FIGS. 5A and B) and average nodule diameter (FIGS. 5C and D).
Figure 5B:
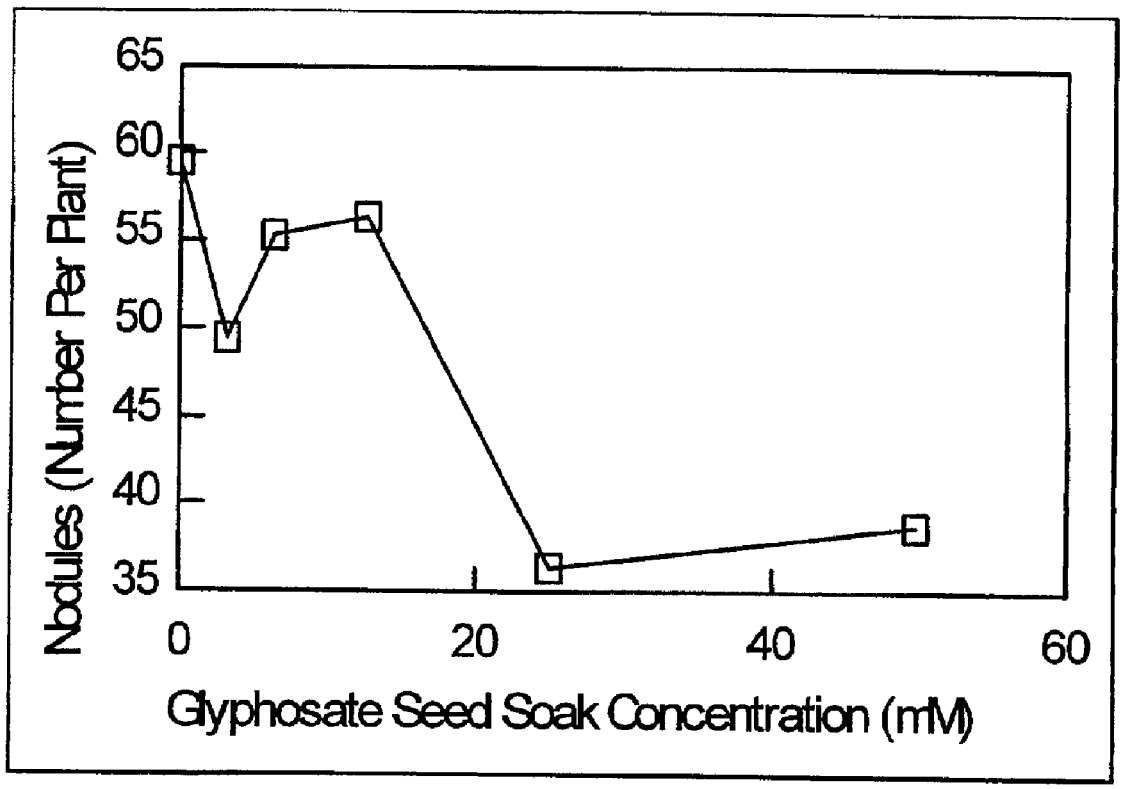
Figure 5C:
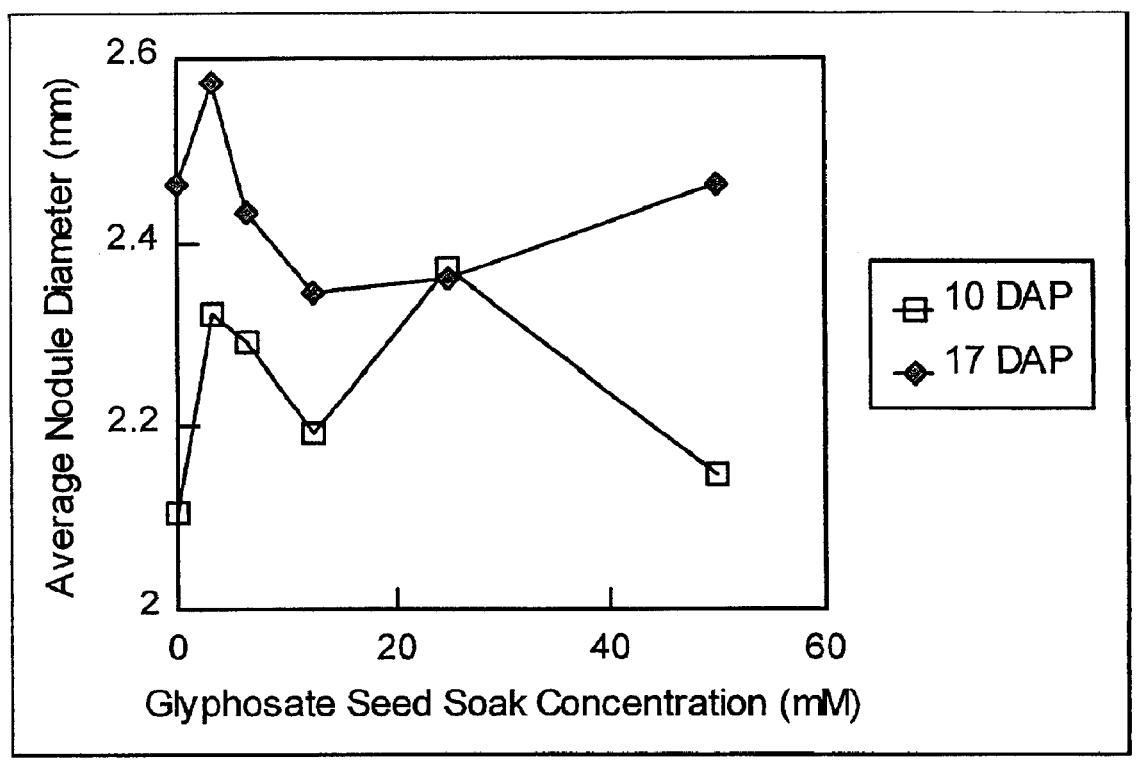
Figure 5D:
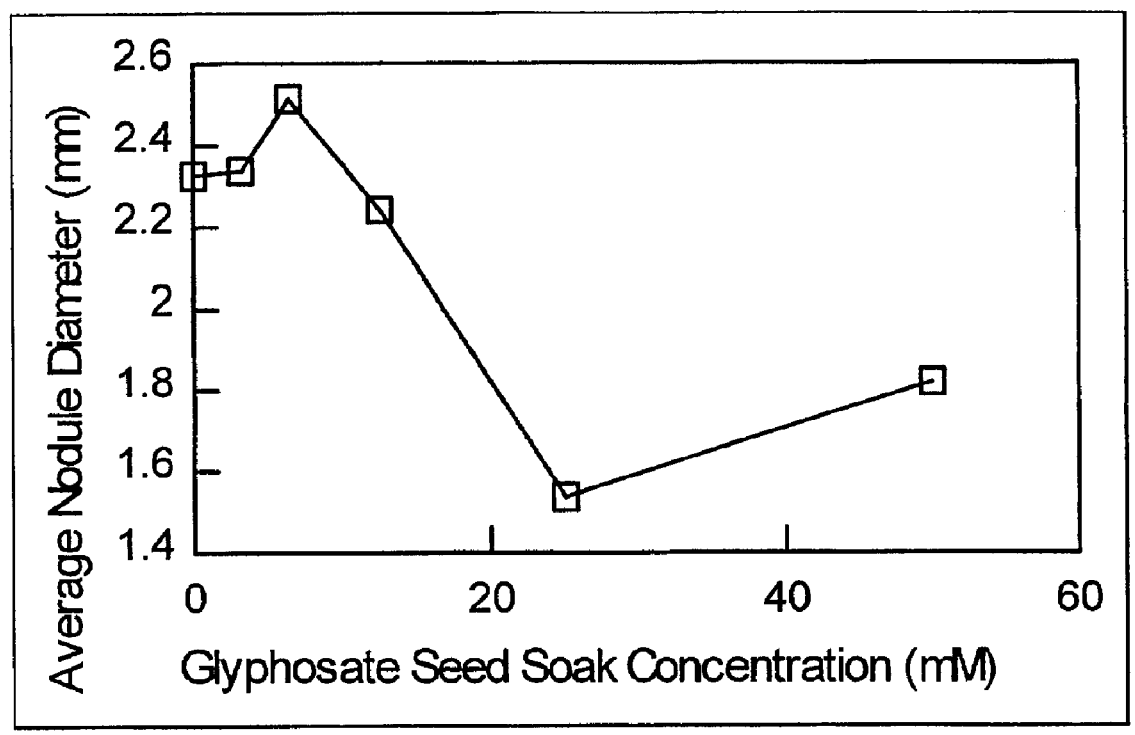

*B. japonicum* (strain USDA 110) was grown in a defined media lacking aromatic amino acids (Karr and Emerich, 1989) on a rotary shaker at 25 C with glyphosate concentrations of 0, 0.01. 0.1, 1, 3, and 5 mM. The optical density at 660 nm of three individual cultures at each glyphosate concentration was measured after 7 days to quantify bacterial growth (Green and Emerich, 1997). At concentrations as low as 0.01 mM, *B. japonicum* growth was inhibited 18% relative to the control (FIG. 4). At a concentration of 0.1 mM, growth was inhibited approximately 40% relative to the control. Importantly, growth inhibition of *B. japonicum* by glyphosate in culture occurred at concentrations that are physiologically relevant and which could inhibit growth of *B. japonicum* during early stages of nodulation. A single foliar application at 0.5 k ha$^{-1}$ of glyphosate results in concentrations up to 0.3 mM in bulk root tissue of susceptible plant species (Honeger et al., 1986). Higher glyphosate application rates or repeated applications would expectantly result in even greater concentrations, especially in the strong metabolic sinks such as soybean root nodules (McWhorter et al., 1980).

Example 13

Seed Treatment as an Alternate Means of Delivering Glyphosate to Plants

To increase the competitiveness of glyphosate resistant *B. japonicum* strains over indigenous species, glyphosate should be in the plant tissues at concentrations inhibitory to nonresistant strains as soon as the radicle emerges from the seed. It has been discovered that soaking seed from glyphosate sensitive soybean cultivars for 2 hours in a 0.4% (v/v) solution of commercial glyphosate (RoundUp Ultra, Monsanto, Co.) completely inhibits plant growth past seedling emergence. For a glyphosate resistant soybean cultivar, soaking seeds for 2 hours in a 3.2% solution of commercial glyphosate had no effect on seedling establishment or early plant growth. Higher dosages of glyphosate to the developing seed is delivered by soaking seeds in greater concentrations of glyphosate or by coating seeds with a dry formulation of glyphosate. The effectiveness of the glyphosate treatments for inhibiting infection by glyphosate-sensitive $B.$ $japonicum$ strains of glyphosate resistant or tolerant soybean is evaluated by monitoring nodulation of soybean two to three weeks after emergence for each of several different dosages of glyphosate on the glyphosate resistant or tolerant seeds.

A greenhouse experiment was conducted to evaluate the effect of seed-imbibed glyphosate solutions on nodulation and nodule development in glyphosate resistant or tolerant soybean during early plant growth. The experiment consisted of six glyphosate concentrations, four replications, and two harvest dates. Solutions of 0, 3.125, 6.25, 12.5, 25, and 50 mM glyphosate were prepared by dissolving technical grade glyphosate (N-(phsophonomethyl)-glycine (Aldrich Chem #33,775-7) in deionized water. One hundred seed, weighing approximately 12 g, of the glyphosate resistant soybean cultivar 'DK5961RR' were placed on filter paper in each of six 10-cm-diameter petri dishes. The filter paper in each petri dish was then wet sufficiently with one of the above mentioned solutions to allow a small amount of standing liquid. Additional solution was added every 15 minutes as needed to maintain a small amount of free liquid during a 2 hour imbibition time. The final weight of the 100 seed after imbibition was approximately 18 g for all glyphosate solutions.

Pots 15-cm in diameter, with a total volume of 1.3 L were filled with a peat based potting mix that was saturated with a nitrogen-free nutrient solution. Six seeds from a particular glyphosate-concentration seed soak were planted in each pot and 1 ml of *B. japonicum* (USDA 110) containing approximately $4.24\times10^6$ cells was applied evenly across the surface and washed into the potting mix with 250 ml of minus N nutrients. Plants were thinned to one per pot after emergence. Day and night temperatures were approximately 30 and 24 C, respectively, and natural illumination was supplemented with 1000 W metal-halide lamps for a day length of 16 hours. Four replications of each glyphosate concentration were harvested at 10 and 17 days after planting and plants were sectioned into nodules, root, and shoot. Root nodules were scanned and images were used to determine nodule number and size as influenced by glyphosate treatment. The equipment was repeated in a controlled environmental growth chamber with six replications. Growth chamber temperature was a constant 25 C and light and dark periods were 16 and 8 hours, respectively. Plants were harvested at 15 days after planting and sectioned as previously described (Example 1).

In the greenhouse experiment, there was an approximate 30% reduction in nodule number at 10 days after planting (DAP) for the 3.1 mM glyphosate treatment compared to the control (FIG. 5A). After an additional week, at 17 DAP, the reduction in nodule number of the 3.1 mM glyphosate treatment was still apparent relative to the control. Similarly, in the growth chamber experiment, there was a decrease in nodule number for the 3.1 mM glyphosate treatment relative to the control at 15 DAP (FIG. 5C).

At glyphosate concentrations greater than 3.1 mM in the greenhouse experiment, nodule number increased to values similar to that of plants from the control treatment (FIG. 5A), but the average diameter of individual nodules tended to decrease at increasing glyphosate concentrations at 17 DAP (FIG. 5B). These same general trends also occurred in the growth chamber experiment except that nodule number from plants at glyphosate concentrations greater than 12 mM progressively decreased (FIGS. 5C and 5D).

In the symbiotic $N_2$ relationship between bacteria and nodulating plants, infection and nodulation continue until an adequate supply of fixed nitrogen in the plant acts as a signal that inhibits further infection and nodule growth (Parsons et al., 1993; Singleton and Stockinger, 1983). Decreased nodule number as observed for the 3 mM glyphosate seed soak (FIGS. 5A and 5C) or increased nodule number and decreased individual nodule weight as occurred with the 6 to 12 mM seed soak in combination with the non-glyphosate resistant strain of USDA 110 at 10 to 17 DAP in the greenhouse experiment would likely decrease the fixed nitrogen supply to the plant during early nodule development. Decreased nitrogen fixation during early plant growth in response in foliar glyphosate applications was evident (Table 5). These data indicate that a wide range of glyphosate concentrations in soybean tissue during early nodule development should give a competitive advantage to glyphosate resistant *B. japonicum* over strains which are not resistant to glyphosate.

Example 14

Relative Stability of Glyphosate Resistance in *B. japonicum*: Introduction of Resistant EPSPS Gene by Integrated into the Bacterial Chromosome or by stable Plasmid Stable integration and expression of the glyphosate resistant EPSPS gene is expected from a double-cross-over event in the bacterial chromosome. Extra-chromosomal transformation of *B. japonicum* with the glyphosate resistant EPSPS gene on a plasmid, however, would likely result in the eventual loss of the plasmid from *B. japonicum* after several generations unless there was continued selection pressure for glyphosate resistance. *B. japonicum* with superior $N_2$ fixation capabilities which is resistant and therefore also has greater competitiveness than indigenous strains, would lose their competitive advantage with the loss of the plasmid. This could require inoculation on a yearly basis.

Plasmid construction is similar to that described in Example 8 with the exception that the constructions are made in a plasmid with a stabilization locus and without flanking homologous regions. A stable plasmid with these characterizations is described by Roberts and Helinski (1992) and has been utilized in nitrogen-fixing bacteria by Kent et al. (1998). Unlike the plasmid described in Example 8 (pRJ1035), plasmids similar to the RK2 plasmid (Roberts and Helinski, 1992) are stable in *B. japonicum* under selection pressure.

After the gene of interests is cloned into a stabilized plasmid, it may be either transformed into *E. coli* (strain S17.1) for biparental mating or used directly for electroporation, as described in Example 8. Screening for transformed bacteria is through selective media containing kanamycin or glyphosate. Additionally, selected colonies can be evaluated by dot-blot hybridization technique described in Example 8.

To determine if the glyphosate resistant EPSPS gene from a plasmid in *B. japonicum* confers resistance and increased competitiveness, plasmid constructs are first evaluated as to the stability of glyphosate resistance in the absence of glyphosate selection pressure. This is accomplished by growing *B. japonicum* in culture in a rich media, such as that described by Vincent (A manual for the practical study of root-nodule bacteria (1970)) which contains the following (g/L): 0.5 $K_2HPO_4$, 0.1 NaCl, 0.2 $MgSO_4$, 0.4 yeast extract, 10 mannitol. Given that *B. japonicum* has a doubling time of approximately 12 h, samples from culture may be taken every other generation over a 7 day period. The approximate cellular number is determined by absorbance at 660 nm. Plasmid stability is determined by plating an equivalent cellular number from each generation on defined media containing 10 mM glyphosate and determining colony forming units. Secondly, the competitive advantage of the plasmid-derived glyphosate resistance of *B. japonicum* is determined as described in Example 10. Thirdly, the loss of the plasmid from bacteria in the symbiotic state is determined by isolating bacteria from nodules of plants inoculated with the plasmid-based glyphosate resistant *B. japonicum*. Cultures are grown on nonselective liquid culture, and plasmid stability is determined by plating an equivalent cellular number from each generation on defined media containing 10 mM glyphosate and determining colony forming units. Although this is a preferred embodiment of the present invention, other means known in the art may be utilized to genetically engineer a resistant rhizobial strain.

While the invention has been disclosed in this patent application by reference to the details of preferred embodiments of the invention, it is to be understood that the disclosure is intended in an illustrative rather than a limiting sense, as it is contemplated that modifications will readily occur to those skilled in the art, within the spirit of the invention and the scope of appended claims.

Bibliography

Acuna et al., 1987. *Plant Mol. Bio.* 9:41–50.
Baltazar and Brotonegoro, 1980. *Phillipp. J. Weed. Sci.* 6:69–80.
Bradshaw et al., 1997. *Weed Technology* 11:189–198.
Cannon et al., 1988. "Nitrogen Fixation: 100 Years After," Bothe et al., Eds., Gustav Fisher, Suttgart, pp. 735–740.
Cooper and Jeffers, 1984. *Agron. J.* 76:257–259.
Crawford et al., 2000. "Nitrogen and sulfur," In Buchanan, B.B., Eds., Biochemistry and Molecular biology of Plants, Am. Soc. of Plant Physiologists, Rockville, Md., pp. 786–849.
Daramola et al., 1994. *Soil Biol. Biochem.* 26(7):883–889.
DeGreef et al., 1989. *Biol. Technology* 7:61.
Delannay et al., 1995. *Crop Science* 35:1461–1467.
Devine and Kuykendall, 1996. *Plant Soil* 186:173–187.
de Silva et al., 1996. *Crop. Sci.* 36:611–616.
Duke, In "Herbicides: Chemistry Degradation and Mode of Action," Kearney et al., Eds., New York, pp. 1–70 (1988).
Durand et al., 1987. *J. Exp. Bot.* 38:311–321.
Erdman et al., 1957. *Agron. J.* 49:267–271.
Fehr and Caviness, 1977. Spec. Report. No. 80, Iowa State Univ. Coop. Ext. Ser., Ames, Iowa.
Fuhrmann and Vasilas, 1994. *Agron. J.* 86:294–298.
Fuhrmann and Vasilas, 1993. *Soil Biol. Biochem.*25: 1203–1209.
Fuhrmann et al., in *Agronomy* abstracts Am. Soc. Agron., Madison, Wisconsin, p. 238 (1996).
Graham et al. in "Principles and applications of soil microbiology," Sylvia et al., Eds., Prentice Hall, Upper Saddle River, N.J., p. 322–345 (1998).
Green and Emerich, 1997. *J. Bacteriol.* 179:194–201.
Guerinot et al., 1990. *Mol. Gen. Genet.* 221:287–290.
Hahn and Hennecke, 1984. *Mol. Gen. Genet.* 193:46–52.
Hayes et al., 1992. *Biochem. J.* 285:173.
Holt et al., in Bergey's Manual of Determinative Bacteriology, 9th Ed., Williams and Wilkins, Baltimore, Md. (1994).
Honegger et al., 1986. In *Phloem* transport, Cronshaw et al., Eds. New York, pp. 609–618 (1986).
Horsch et al., 1988. *Iowa State J. Res.* 62:487–502.
Jacob et al., 1988. *Appl. Environ. Microbiol.* 54:2953 Agr. Food. Chem. 20:1195–1198.
Johnson and Means, 1960. *Agron. J.* 52:651–654.
Kanehisa, 1984. *Nucl. Acids Res.* 12:203–213.
Karr and Emerich, 1989. *J. Bacteriol.* 171:3420–3426.
Kent et al., 1998. *Appl. Environ. Microbiol.* 64:1654–1662.
Jaworski, 1972. *J. Agron. J.* 93:179–186.
Kuykendall et al., 1996. *Plant Soil* 186:121–125.
Lafavre and Eaglesham, 1986. *Plant Soil* 92:443–452.
Lang et al., 1982. *Nature* 298:485–488.
Lee et al., 1988. *EMBO J.* 7:1241.
Loh et al., 1999. *J. Bacteriol.* 181:1544–1554.
Maier and Triplett, 1996. *Crit. Rev. Plant Sci.* 15:191–234.
Marshall et al., 1992. *Theor. Appl. Genet.* 83:435.
McWhorter et al., 1980. *Weed Sci.* 28:113–118.
Miki et al., 1990. *Theor. Appl. Genet.* 80:449.
Minchin et al., 1983. *J. Exp. Bot.* 34:641–649.
Moorman et al., 1992. *J. Agric. Food Chem.* 40:289–293.
Owens and Wright, 1965. *Plant Physiol.* 40:927–930.
Padgette et al., 1995. *Crop Science* 35:1451–1461.
Parsons et al., 1993. *Plant Cell. Environ.* 16:125–136.
Pipke et al., 1988. *Appl. Environ. Microbiol.* 54:1293–1296.
Przibilla et al., 1991. *Plant Cell* 3:169.
Purcell et al., 1997. *Plant Soil* 196:101–113
Purcell et al., 2000. *Crop Sci.* 40:1062–1070.
Purcell and King, 1996. *J. Plant Nutr.* 19:969–993.
Ray and Sinclair, 1997. *Crop. Sci.* 37:803–807.
Ritchie, 1981. *Plant Soil* 58:81–96.
Roberts and Helinski, 1992. *J. Bacteriol.* 174:8119–8132.
Sall and Sinclair, 1991. *Plant Soil* 133:31–37.
Sallam and Scott, 1987. *Soil Sci.* 144:61–66.
Scott et al., 1989. *Agron. J.* 81:631–636.
Singleton and Stockinger, 1983. *Crop Sci.* 23:69–72.
Spaink et al., 1989. *J. Bacteriol.* 171:4045–4053.
Southern, 1975. *J. Mol Biol.* 98:503–517.
Talbott et al., 1985. *Field Crops. Res.* 11:55–67.
Teaney and Fuhrmann, 1993. *Plant Soil* 154:219–225.
Udvardi and Day, 1997. *Annu. Rev. Plant Physiol. Plant Mol. Biol.* 48:493–523.
Vasilas and Fuhrmann, 1993. *Agron. J.* 85:302–305.
Weaver and Frederick, 1974. *Agron. J.* 66:229–232.
Wetmur and Davidson, 1968. *J. Mol. Biol.* 31:349–370.
Vasilas and Fuhrmann, 1993. *Crop Sci.* 33:785–787.

Patents and Patent Applications

U.S. Pat. No. 4,720,461
U.S. Pat. No. 4,769,061
U.S. Pat. No. 4,810,648
U.S. Pat. No. 4,863,866
U.S. Pat. No. 4,940,835
U.S. Pat. No. 4,971,908
U.S. Pat. No. 4,975,374
U.S. Pat. No. 5,021,076
U.S. Pat. No. 5,045,461
U.S. Pat. No. 5,094,945
U.S. Pat. No. 5,173,424
U.S. Pat. No. 5,308,616
U.S. Pat. No. 5,776,760

U.S. Pat. No. 5,922,316
U.S. Pat. No. 5,998,700
U.S. Pat. No. 6,040,270
European patent application No. 0 333 033
European patent application No. 0 242 246

What is claimed is:

1. A method for enhancing nodulation of nodulating leguminous plants, wherein said plant displays resistance or tolerance to glyphosate herbicide, comprising:
    a) growing said plant in the field in the presence of a rhizobial strain wherein said rhizobial strain comprises resistance to said glyphosate herbicide; and
    b) applying said glyphosate herbicide to said leguminous plant or seeds of said plant, whereby nodulation by the desired strain expresses resistance or tolerance to glyphosate and is enhanced compared to nodulation by a strain that is not resistant to the herbicide glyphosate.

2. The method of claim 1, wherein said rhizobial strain is obtained by a genetic engineering.

3. The method of claim 1, wherein said herbicide is applied according to a method selected from the group consisting of application to the plant and application to seeds of said plant.

4. The method of claim 1, wherein said rhizobial strain is administered by a method selected from the group consisting of application to the seeds of the plant, application to the plant, application to the locus of the plant root, and application by in-furrow spray.

5. The method of claim 1, wherein said herbicide is applied to said plant by a method selected from the group consisting of application before administering the rhizobial strain, application simultaneously with administering the rhizobial strain, and application after administering said rhizobial strain.

6. The method of claim 1, wherein said rhizobial strain is selected from a group consisting of *Bradyrhizobium japonicum, Bradyrhizobium elkanii, Sinorhizobium fredii, Sinorhizobium meliloti, Sinorhizobium* sp. NGR234, *Rhizobium leguminosarum* biovar *viciae, R. leguminosarum* biovar *trifolii, R. leguminosarum* biovar *phaseoli, R. tropici, R. etli, Mesorhizobium loti, B. elkani* and *Azorhizobium caulinodans*.

7. The method of claim 6, wherein said rhizobial strain is *Bradyrhizobium japonicum*.

8. The method of claim 1, wherein said nodulating leguminous plant is selected from the group consisting of soybean, cowpea, alfalfa, chickpea, bean, pigeonpea, sweetclover, trefoil, siratro, sweet pea, pea, vetch and clover.

9. The method of claim 8, wherein the nodulating leguminous plant is a soybean plant.

10. The method of claim 1, wherein said rhizobial strain further comprises a superior dinitrogen fixing strain, and wherein said rhizobial strain displays enhanced competitiveness.

11. The method of claim 10, wherein said rhizobial strain is obtained by genetic engineering.

12. The method of claim 10, wherein said herbicide is applied according to a method selected from the group consisting of application to the plant and application to seeds of said plant.

13. The method of claim 10, wherein said rhizobial strain is administered by a method selected from the group consisting of application to the seeds of the plant, application to the plant, application to the locus of the plant root, and application by in-furrow spray.

14. The method of claim 10, wherein said herbicide is applied to said plant by a method selected from the group consisting of application before administering the rhizobial strain, application simultaneously with administering the rhizobial strain, and application after administering said rhizobial strain.

15. The method of claim 10, wherein said rhizobial strain is selected from a group consisting of *Bradyrhizobium japonicum, Bradyrhizobium elkanii, Sinorhizobium fredii, Sinorhizobium meliloti, Sinorhizobium* sp. NGR234, *Rhizobium leguminosarum* biovar *viciae, R. leguminosarum* biovar *trifolii, R. leguminosarum* biovar *phaseoli, R. tropici, R. etli, Mesorhizobium loti, B. elkani* and *Azorhizobium caulinodans*.

16. The method of claim 15, wherein said rhizobial strain is *Bradyrhizobium japonicum*.

17. The method of claim 10, wherein said nodulating leguminous plant is selected from the group consisting of soybean, cowpea, alfalfa, chickpea, bean, pigeonpea, sweetclover, trefoil, siratro, sweet pea, pea, vetch and clover.

18. The method of claim 17, wherein the nodulating leguminous plant is a soybean plant.

19. A method of enhancing dinitrogen fixation of a nodulating leguminous plant comprising:
    a) inoculating said plant or seed of said plant with a rhizobial strain, said rhizobial strain comprising resistance to glyphosate herbicide;
    b) applying said glyphosate herbicide to said leguminous plants, wherein said plant is resistant or tolerant to the herbicide; and
    c) growing the leguminous plant in symbiotic relationship with the rhizobial strain thereby enhancing dinitrogen fixation of a nodulating leguminous plant.

20. The method of claim 19, wherein said resistant rhizobial strain enhances dinitrogen fixation as compared to a rhizobial strain which is not resistant to said herbicide of interest.

21. The method of claim 19, wherein said rhizobial strain is selected from a group consisting of *Bradyrhizobium japonicum* subspecies 1, *Bradyrhizobium elkanii, Sinorhizobium fredii, Sinorhizobium meliloti, Sinorhizobium* sp. NGR234, *Rhizobium leguminosarum* biovar *viciae, R. leguminosarum* biovar *trifolii, R. leguminosarum* biovar *phaseoli, R. tropici, R. etli, Mesorhizobium loti, B. elkani* and *Azorhizobium caulinodans*.

22. The method of claim 19, wherein said herbicide is applied according to a method selected from the group consisting of application to the plant and application to seeds of the plant.

23. The method of claim 19, wherein said inoculating is by a method selected from the group consisting of application to the plant, application to locus of the plant roots, application to seeds of the plant, and application by in-furrow spray.

24. The method of claim 19, wherein the application of said herbicide is by a mode selected from the group consisting of application before inoculating the plant, application simultaneously with inoculating the plant, and application after inoculating the plant with the rhizobia.

25. The method of claim 19, wherein said rhizobial strain further comprises a superior dinitrogen fixing strain.

26. The method of claim 19, wherein said leguminous plant is selected from the group consisting of soybean plant, cowpea, alfalfa, chickpea, bean, pigeonpea sweetclover, Siratro, sweet pea, pea, vetch and clover.

27. The method of claim 26, wherein said leguminous plant is soybean.

28. A glyphosate resistant rhizobial strain, wherein said resistant rhizobial strain has been obtained by genetic engineering.

29. A plant infected by the glyphosate resistant rhizobial strain of claim 28.

* * * * *